(12) United States Patent
Kashfi et al.

(10) Patent No.: US 10,023,555 B2
(45) Date of Patent: Jul. 17, 2018

(54) NSAIDS DERIVATIVES AND USES THEREOF

(71) Applicant: Research Foundation of The City University of New York, New York, NY (US)

(72) Inventors: Khosrow Kashfi, Dix Hills, NY (US); Mitali Chattopadhyay, New York, NY (US); Ravinder Kodela, New York, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 80 days.

(21) Appl. No.: 14/766,258

(22) PCT Filed: Feb. 7, 2014

(86) PCT No.: PCT/US2014/015222
§ 371 (c)(1),
(2) Date: Aug. 6, 2015

(87) PCT Pub. No.: WO2014/124208
PCT Pub. Date: Aug. 14, 2014

(65) Prior Publication Data
US 2015/0376162 A1 Dec. 31, 2015

Related U.S. Application Data

(60) Provisional application No. 61/761,848, filed on Feb. 7, 2013.

(51) Int. Cl.
| C07F 9/09 | (2006.01) |
| C07F 9/6574 | (2006.01) |
| C07D 339/04 | (2006.01) |
| C07F 9/6553 | (2006.01) |

(52) U.S. Cl.
CPC ............. C07D 339/04 (2013.01); C07F 9/09 (2013.01); C07F 9/091 (2013.01); C07F 9/65742 (2013.01); C07F 9/655345 (2013.01)

(58) Field of Classification Search
CPC ......... C07F 9/09; C07F 9/091; C07F 9/65742
See application file for complete search history.

(56) References Cited

U.S. PATENT DOCUMENTS

| 6,482,811 B1 | 11/2002 | Bacaner et al. |
| 2005/0182134 A1 | 8/2005 | Kashfi |
| 2006/0046967 A1 | 3/2006 | Satyam |
| 2006/0205674 A2 * | 9/2006 | Satyam ................ A61K 47/481 514/1.1 |
| 2009/0099137 A1 | 4/2009 | Rigas |
| 2013/0225529 A1 * | 8/2013 | Rigas ................... A61K 31/661 514/91 |

FOREIGN PATENT DOCUMENTS

| WO | WO2011130486 A2 | 10/2011 |
| WO | WO2011130486 A2 | 10/2011 |

OTHER PUBLICATIONS

Ohsako et al. "Modeling of Controlled Release of Aspirin Derivatives from Human Erythrocytes" Biological and Pharmaceutical Bulletin, 1995, vol. 18, No. 2, pp. 310-314.*
Azema et al., "Cell Permeation of a Trypanosoma Brucei Aldolase Inhibitor: Evaluation of Different Enzyme-Labile Phosphate Protecting Groups", Bioorganic & Medicinal Chemistry Letters 16(13), 3440-3443 (2006).
Nemmai et al., "NO-NSAIDs: Gastric-Sparing Nitric Oxide-Releasable Prodrugs of Non-Steroidal Anti-Inflammatory Drugs", Bioorganic & Medicinal Chemistry Letters, 19(18), 5297-5301 (2009).
Supplemental Partial European Search Report for corresponding European Patent Application No. EP14748566, dated Oct. 28, 2015, pp. 1-7.
International Search Report for corresponding PCT Application No. PCT/US2014/015222, pp. 1-3 (dated Jul. 18, 2014).

* cited by examiner

*Primary Examiner* — Joseph R Kosack
(74) *Attorney, Agent, or Firm* — Hoffmann & Baron, LLP

(57) ABSTRACT

The present invention discloses novel compounds derived from NSAIDs and pharmaceutically acceptable salts thereof. Other aspects of the invention relate to use of the NSAID derivatives in treating inflammatory diseases and pharmaceutical compositions thereof.

12 Claims, No Drawings

NSAIDS DERIVATIVES AND USES THEREOF

CROSS-REFERENCE TO RELATED APPLICATION

The present application claims the benefit of PCT Application No. PCT/US14/15222, filed Feb. 7, 2014, which claims the benefit of U.S. Provisional Patent Application No. 61/761,848, filed on Feb. 7, 2013. The entire contents of which are hereby incorporated by reference.

BACKGROUND OF THE INVENTION

Non-steroidal anti-inflammatory drugs (NSAIDs) are prototypical agents for treatment of inflammatory conditions. NSAIDs may also have utility as therapeutic agents against many forms of cancers. However, long-term use of NSAIDs may lead to serious side effects affecting the gastrointestinal and renal systems.

Recognition that endogenous gaseous mediators, nitric oxide (NO) and hydrogen sulfide ($H_2S$) can increase mucosal defense mechanisms has led to the development of NO-releasing NSAIDs and $H_2S$-releasing NSAIDs with increased safety profiles. NO-NSAIDs and HS-NSAIDs, however, have several drawbacks. HS-NSAIDs, for example, have relatively high $IC_{50}$s for cell growth inhibition. Some NO-NSAIDs can form quinone methide intermediates, raising doubts about the role of NO in their biological activity. Other NO-NSAIDs have high $IC_{50}$s for cell growth inhibition.

Hybrid dual action compounds that incorporate both NO and $H_2S$ donor components were found to be more potent therapeutic agents than compounds that donate only one of these groups. Such dual action compounds provide improved safety and methods of treatment of inflammatory conditions, such as cancers. Khosrow Kashfi and Ravinder Kodela disclosed some of these compounds in International Publication No. WO 2013/025790 (International Application No. PCT/US2012/050922), the contents of which are incorporated herein in its entirety.

However, there remains a need for additional NSAID derivatives bearing moieties that provide activity against inflammatory conditions, such as cancer, rheumatoid arthritis, intestine inflammation, stomach ulcer, cardiovascular disease, and neurodegenerative disease.

SUMMARY OF THE INVENTION

The present invention relates to compounds of the general formulas with activity towards treating diseases related to inflammation, such as, gastrointestinal diseases, cancer, and cardiovascular diseases.

In one embodiment, the invention relates to a compound of Formula I:

(I)

wherein:
R is a non-steroidal anti-inflammatory drug (NSAID) or $R^1$—C(O)—$X^1$—;
$R^1$ is an alkyl, cycloalkyl, or aryl;
$X^1$ is O, S, or NH;
X is an alkyl, a cycloalkyl, an aryl, or —$(CH_2)_{n1}$—$S_{n2}$—$(CH_2)_{n1}$—;
n1 is independently an integer from 1 to 20;
n2 is 2, 3, or 4;

Y is independently —OP(O)(OEt)$_2$,

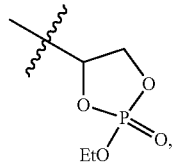

—$OSO_2R^2$, —$OSO_2OR^2$, —$OB(OR^2)_2$, halo, an $H_2S$ releasing moiety, or an NO releasing moiety;
$R^2$ is independently —$(CH_2)_{n1}$—H;
alkyl groups are branched or unbranched, saturated or unsaturated, and have 1-20 carbon atoms in their longest chain;
aryl groups are carbocyclic or heterocyclic;
aryl groups may be unsubstituted or substituted with one or more substituent at any position;
cycloalkyl groups are carbocyclic or heterocyclic, fused or unfused, non-aromatic ring systems having a total of 3-16 ring members including substituent rings;
each alkyl or cycloalkyl, independently, may be unsubstituted or substituted with one or more substituent at any position;
alkyl substituents are halo, hydroxyl, $OR^3$, $SR^3$, $NH_2$, $NHR^3$, cycloalkyl, or aryl;
cycloalkyl substituents are halo, hydroxyl, $OR^3$, $SR^3$, $NH_2$, $NHR^3$, alkyl, cycloalkyl, or aryl;
aryl substituents are halo, hydroxyl, $OR^3$, $SR^3$, $NH_2$, $NHR^3$, alkyl, cycloalkyl, aryl, nitro, carboxyl, or —O—C(O)-alkyl;
heterocyclic alkyl and aryl groups have at least one heteroatom selected from oxygen, nitrogen, and sulfur;
$R^3$ represents alkyl, cycloalkyl, aryl, or halo; and
halo substituents are fluoro, chloro, or bromo.

In another embodiment, the invention relates to a compound of Formula II:

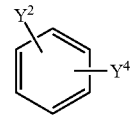
(II)

wherein:
$Y^2$ is $Y^3$, —C(O)—$X^1$—$X_{n4}$—Y or —$X^1$—$X_{n4}$—Y;
$Y^4$ is —C(O)—$X^1$—$X_{n4}$—Y or —$X^1$—$X_{n4}$—Y;
$R^2$ is —$(CH_2)_{n1}$—H;
$X^1$ is O, S, or NH;
X is an alkyl, a cycloalkyl, an aryl, or —$(CH_2)_{n1}$—$S_{n2}$—$(CH_2)_{n1}$—;
Y is independently —OP(O)(OEt)$_2$,

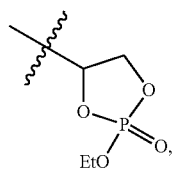 [SMILES: *C1COP(=O)(OCC)O1]

—$OSO_2R^2$, —$OSO_2OR^2$, —$OB(OR^2)_2$, halo, an $H_2S$ releasing moiety, or an NO releasing moiety;

$Y^3$ is an $H_2S$ releasing moiety or an NO releasing moiety;
$n1$ is independently an integer from 1 to 20;
$n2$ is 2, 3, or 4;
$n4$ is 0 or 1;
alkyl groups are branched or unbranched, saturated or unsaturated, and have 1-20 carbon atoms in their longest chain;
aryl groups are carbocyclic or heterocyclic;
aryl groups may be unsubstituted or substituted with one or more substituent at any position;
cycloalkyl groups are carbocyclic or heterocyclic, fused or unfused, non-aromatic ring systems having a total of 3-16 ring members including substituent rings;
each alkyl or cycloalkyl, independently, may be unsubstituted or substituted with one or more substituent at any position;
alkyl substituents are halo, hydroxyl, $OR^3$, $SR^3$, $NH_2$, $NHR^3$, cycloalkyl, or aryl;
cycloalkyl substituents are halo, hydroxyl, $OR^3$, $SR^3$, $NH_2$, $NHR^3$, alkyl, cycloalkyl, or aryl;
aryl substituents are halo, hydroxyl, $OR^3$, $SR^3$, $NH_2$, $NHR^3$, alkyl, cycloalkyl, aryl, nitro, carboxyl, or —O—C(O)-alkyl;
heterocyclic alkyl and aryl groups have at least one heteroatom selected from oxygen, nitrogen, and sulfur;
$R^3$ represents alkyl, cycloalkyl, aryl, or halo; and
halo substituents are fluoro, chloro, or bromo.

In another embodiment, the invention relates to a compound of Formula III:

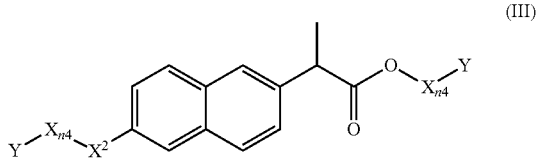

wherein:
$X^2$ is O, —C(O)—O—, or —O—C(O)—;
X is independently an alkyl, a cycloalkyl, an aryl, or —$(CH_2)_{n1}$—$S_{n2}$—$(CH_2)_{n1}$—;
Y is independently —OP(O)(OEt)$_2$,

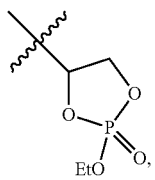 [SMILES: *C1COP(=O)(OCC)O1]

—$OSO_2R^2$, —$OSO_2OR^2$, —$OB(OR^2)_2$, halo, an $H_2S$ releasing moiety, or an NO releasing moiety;
$R^2$ is —$(CH_2)_{n1}$—H;
$n1$ is independently an integer from 1 to 20;
$n2$ is 2, 3, or 4;
$n4$ is 0 or 1;
alkyl groups are branched or unbranched, saturated or unsaturated, and have 1-20 carbon atoms in their longest chain;
aryl groups are carbocyclic or heterocyclic;
aryl groups may be unsubstituted or substituted with one or more substituent at any position;
cycloalkyl groups are carbocyclic or heterocyclic, fused or unfused, non-aromatic ring systems having a total of 3-16 ring members including substituent rings;
each alkyl or cycloalkyl, independently, may be unsubstituted or substituted with one or more substituent at any position;
alkyl substituents are halo, hydroxyl, $OR^3$, $SR^3$, $NH_2$, $NHR^3$, cycloalkyl, or aryl;
cycloalkyl substituents are halo, hydroxyl, $OR^3$, $SR^3$, $NH_2$, $NHR^3$, alkyl, cycloalkyl, or aryl;
aryl substituents are halo, hydroxyl, $OR^3$, $SR^3$, $NH_2$, $NHR^3$, alkyl, cycloalkyl, aryl, nitro, carboxyl, or —O—C(O)-alkyl;
heterocyclic alkyl and aryl groups have at least one heteroatom selected from oxygen, nitrogen, and sulfur;
$R^3$ represents alkyl, cycloalkyl, aryl, or halo; and
halo substituents are fluoro, chloro, or bromo.

In another embodiment, the invention relates to a method of treating an inflammatory disease, comprising administering to a subject in need thereof, an effective amount of a compound of Formula I, II, or III.

In yet another embodiment, the invention relates to a pharmaceutical composition comprising a compound of Formula I, II, or III, and a pharmaceutically acceptable carrier.

DETAILED DESCRIPTION

The invention relates to novel NSAID derivatives of Formulas I, II, and III and the novel NSAID derivatives shown in Table I. These NSAID derivatives can be used to treat inflammatory conditions, such as, gastrointestinal diseases, cancer, and cardiovascular diseases.

One embodiment of the invention is Formula I, shown below:

R—X—Y    (I).

In Formula I, R represents a non-steroidal anti-inflammatory drug (NSAID) or $R^1$—C(O)—$X^1$—. NSAIDs are a well known class of drugs. Some examples of NSAIDs include Aspirin, Naproxen, Sulindac, Ibuprofen, Indomethacin, Valproic acid, Fenamic acid, Flurbiprofen, Diclofenac, Diflunisal, Salsalate, Choline Magnesium Trisalicylate, Dexibuprofen, Fenoprofen, Detoprofen, Dexketoprofen, Oxaprozin, Loxoprofen, Tolmetin, Etodolac, Ketorolac, Aceclofenac, Nabumetone, Piroxicam, Meloxicam, Tenoxicam, Droxicam, Lornoxicam, Isoxicam, Mefenamic acid, Meclofenamic acid, Flufenamic acid, Tolfenamic acid, Selective COX-2 inhibitors, and Licofelone. Preferred NSAIDs include Aspirin, Naproxen, Sulindac, Ibuprofen, Indomethacin, Valproic acid, Fenamic acid, Flurbiprofen, and Diclofenac.

$R^1$ represents an alkyl, cycloalkyl, or aryl.

Alkyl groups are branched or unbranched, saturated or unsaturated, and have 1-20 carbon atoms in their longest chain. Some examples of suitable straight-chained, saturated alkyl groups include methyl, ethyl, n-propyl, n-butyl, n-pentyl, n-hexyl groups, dodecyl, hexadecyl, and icosyl. Preferred straight chain, saturated alkyl groups include methyl and ethyl.

Some examples of suitable branched, saturated alkyl groups include iso-propyl, iso-butyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl (neopentyl), 1-methylpentyl, 2-methylpentyl, 3-methylpentyl, 4-methylpentyl groups, and 2-methyl, 5-ethyldecyl. Preferred branched, saturated alkyl groups include isopropyl and t-butyl.

Some examples of unsaturated alkyl groups include ethenyl, ethynyl, propenyl, propargyl, isopropenyl, crotyl, 1-hexenyl, and 1-octenyl.

Cycloalkyl groups are carbocyclic or heterocyclic, fused or unfused, non-aromatic ring systems having a total of 3-16 ring members including substituent rings. Ring systems are monocyclic, bicyclic, tricyclic, or tetracyclic and can be bridged or non-bridged.

Some examples of carbocyclic alkyl groups include cyclopropanyl, cyclobutanyl, cyclopentanyl, cyclohexanyl, and cycloheptanyl. Examples of fused carbocyclic alkyl groups include indenyl, isoindenyl. Bridged groups include bicyclo[2.2.1]heptane, bicycico[5.2.0]nonane, and bicyclo[5.2.0]nonane.

Some examples of heterocyclic alkyl groups include pyrrolidinyl, piperidinyl, piperazinyl, tetrahydrofuranyl, morpholino, and oxazolidinyl. Examples of fused heterocyclic alkyl groups include benzomorpholino, benzopyrrolidinyl, indolinyl, and benzopiperidinyl.

Aryl groups can be either carbocyclic or heterocyclic.

Carbocyclic aryl groups are fused or unfused ring systems having a total of 6-16 ring members including substituent rings. A preferred unfused carbocyclic aryl group is phenyl.

Some examples of fused carbocyclic aryl groups include naphthyl, phenanthryl, anthracenyl, triphenylenyl, chrysenyl, and pyrenyl.

Heterocyclic aryl groups are fused or unfused ring systems having a total of 5-16 ring members including substituent rings.

Some examples of unfused heterocyclic aryl groups include thiophenyl, furyl, pyrrolyl, pyrazolyl, imidazolyl, oxazolyl, thiazolyl, pyridinyl, pyridazinyl, pyrimidinyl, and pyrazinyl. Some examples of fused heterocyclic aryl groups include purinyl, 1,4-diazanaphthalenyl, indolyl, benzimidazolyl, 4,5-diazaphenanthrenyl, benzoxazolyl, isoindolyl, quinolinyl, isoquinolinyl, and benzofuranyl.

Halo substituents are fluoro, chloro, and bromo.

Each alkyl, cycloalkyl, and aryl, independently, may be unsubstituted or substituted with one or more substituent at any position. Alkyl substituents are halo, hydroxyl, $OR^3$, $SR^3$, $NH_2$, $NHR^3$, cycloalkyl, or aryl. Cycloalkyl substituents are halo, hydroxyl, $OR^3$, $SR^3$, $NH_2$, $NHR^3$, alkyl, cycloalkyl, or aryl. Aryl substituents are halo, hydroxyl, $OR^3$, $SR^3$, $NH_2$, $NHR^3$, alkyl, cycloalkyl, aryl, nitro, carboxyl, or —O—C(O)— alkyl.

Heterocyclic alkyl and heterocyclic aryl have at least one heteroatom selected from oxygen, nitrogen, and sulfur.

$R^3$ represents alkyl, cycloalkyl, aryl, or halo.

$X^1$ represents O, S, or NH. Preferably, $X^1$ is O.

X is a chain represented by an alkyl, a cycloalkyl, an aryl, or —(CH$_2$)$_{n1}$—S$_{n2}$—(CH$_2$)$_{n1}$—. X is preferably —(CH$_2$)—(CH$_2$)—S—S—(CH$_2$)—(CH$_2$)—, —(CH$_2$)—(CH$_2$)—S—S—S—(CH$_2$)—(CH$_2$)—, —(CH$_2$)—(CH$_2$)—S—S—S—S—(CH$_2$)—(CH$_2$)—, or —(CH$_2$)$_4$—.

A chain is defined as a chemical moiety bonded independently at each end to another chemical moiety, e.g., to a group, or to an atom. For example, if X is an alkyl, then the chain could be represented by —CH$_2$—CH$_2$—CH$_2$—CH$_2$—CH$_2$— or —CH$_2$—CH$_2$—CH$_2$—. If X is an aryl, then X could be represented by, for example,

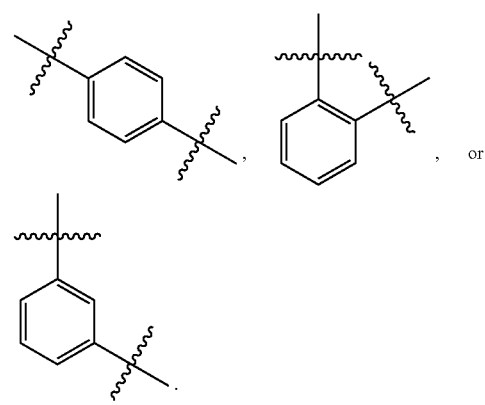

Some examples of cycloalkyl chains are below:

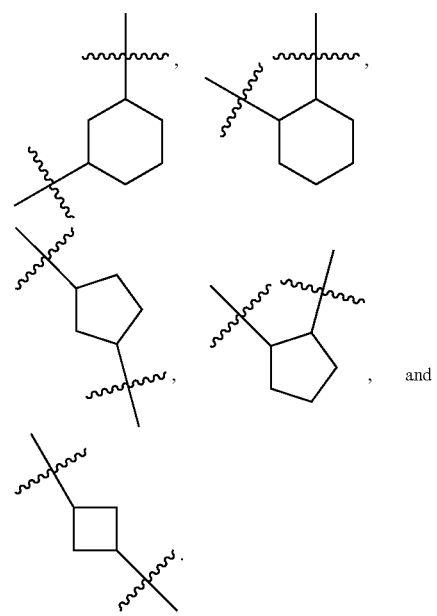

n1 independently represents an integer from 1 to 20, i.e., 1, 2, 3, 4, 5, 6, 7, 8, 9, 10, 11, 12, 13, 14, 15, 16, 17, 18, 19, or 20. Preferably, n1 is 2.

n2 represents 2, 3, or 4. Preferably, n2 is 2.

Y independently represents —OP(O)(OEt)$_2$,

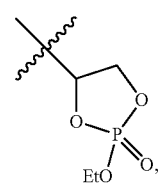

—OSO$_2$R$^2$, —OSO$_2$OR$^2$, —OB(OR$^2$)$_2$, halo, an H$_2$S releasing moiety, or an NO releasing moiety. Preferably, Y represents —OP(O)(OEt)$_2$, an H$_2$S releasing moiety, or an NO releasing moiety.

H$_2$S releasing moieties and NO releasing moieties are well known in the art. As used herein, "a H$_2$S-releasing moiety" refers to a moiety that can be cleaved from a parent compound to generate H₂S under physiological conditions after the parent compound is administered to a patient. Some examples of H₂S releasing moieties include
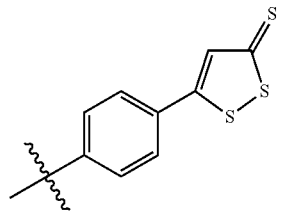,
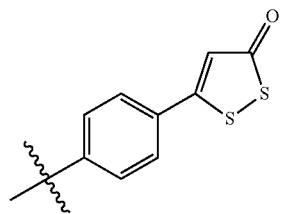,
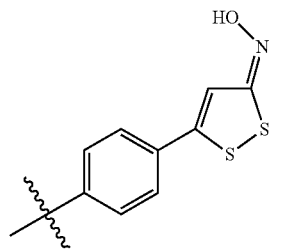,
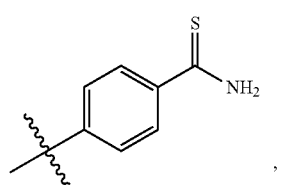,
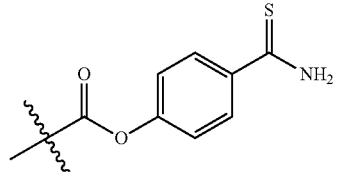,
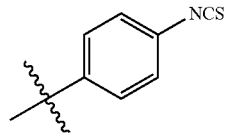,
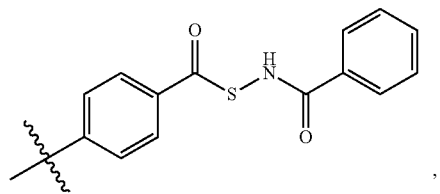,
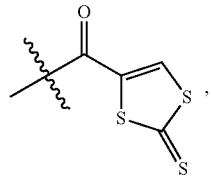,
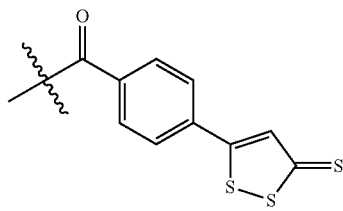,
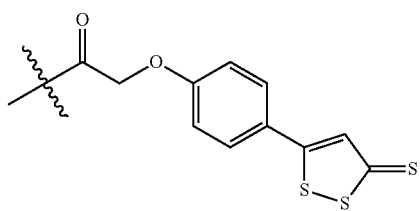,
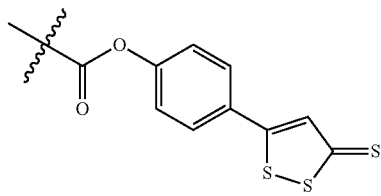,
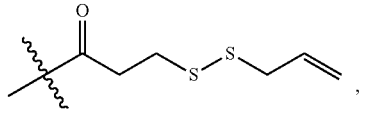,
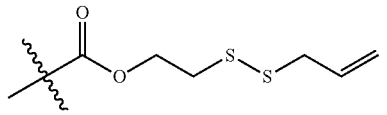,
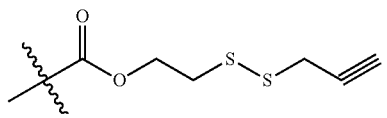,
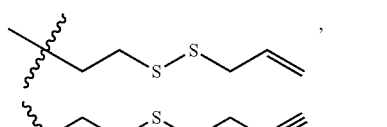,
,
,
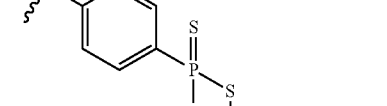,
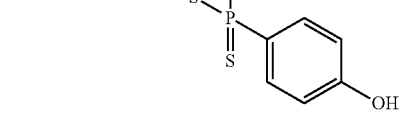,

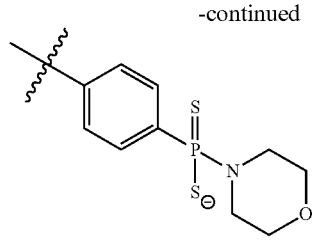

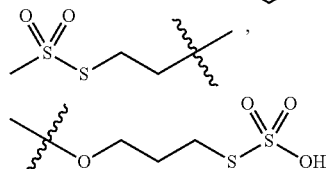

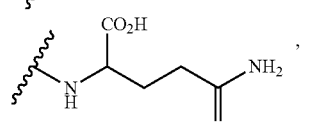

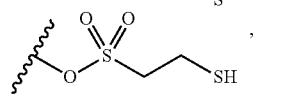

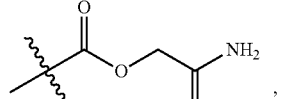

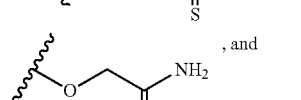

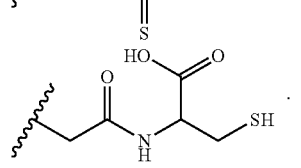

As used herein, "a NO-releasing moiety" refers to a moiety that can be cleaved from a parent compound to generate NO under physiological conditions after the parent compound is administered to a patient. Some examples of NO releasing moieties include —NO, —ONO$_2$, —C(O)—(CH$_2$)$_{n3}$—ONO$_2$, —O—(CH$_2$)$_{n3}$—ONO$_2$, —(CH$_2$)$_{n3}$—ONO$_2$, —C(O)—CH$_2$—C(CH$_3$)$_2$—SNO, —NH—CH$_2$—C(CH$_3$)$_2$—SNO, —CH$_2$—C(CH$_3$)$_2$—SNO,

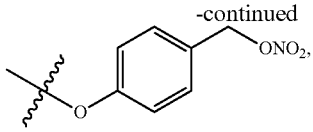

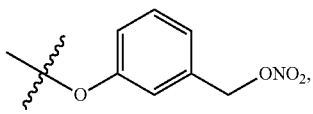

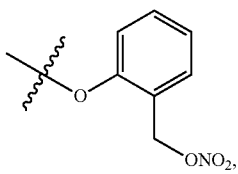

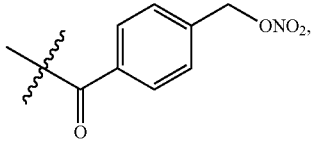

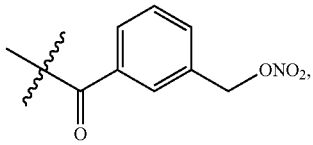

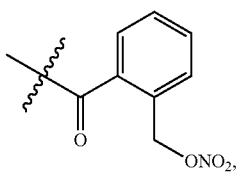

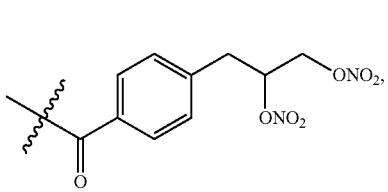

-continued

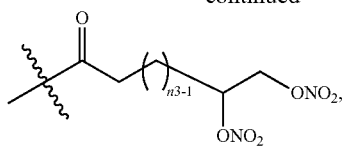
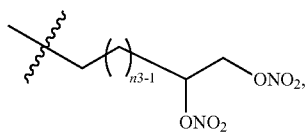
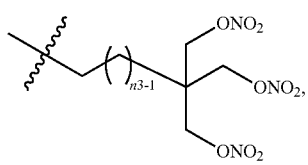
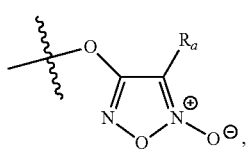
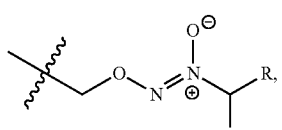
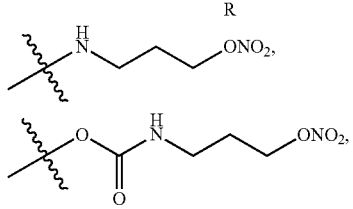
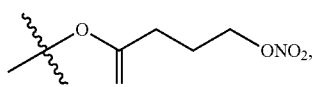
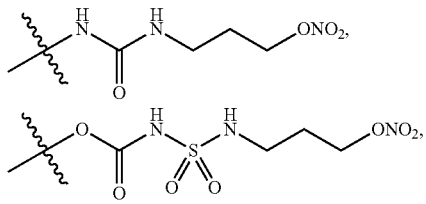
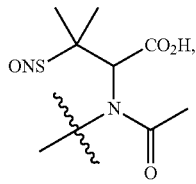

-continued

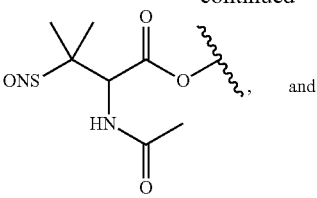 and

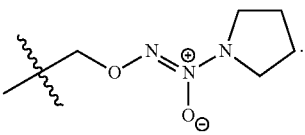

n3 represents 1, 2, 3, 4, 5, 6, or 7.

$R_a$ represents H, $C_1$-$C_{10}$ alkyl, aryl, $S(O)_2$-aryl, CN, or $CON(R_b)_2$. $C_1$-$C_{10}$ alkyl groups are alkyl groups with 1-10 carbon atoms in their longest chain.

$R_b$ independently represents H or $C_1$-$C_{10}$ alkyl.

$R^2$ is independently —$(CH_2)_{n1}$—H.

Another embodiment of the invention is Formula II, shown below:

(II)

$Y^2$ represents $Y^3$, —C(O)—$X^1$—$X_{n4}$—Y, or —$X^1$—$X_{n4}$—Y.

$Y^4$ represents —C(O)—$X^1$—$X_{n4}$—Y or —$X^1$—$X_{n4}$—Y.

X, $X^1$, Y, n1, and n2 are as described above.

$Y^3$ represents an $H_2S$ releasing moiety or an NO releasing moiety. $H_2S$ releasing moieties and NO releasing moieties are described above.

n4 represents 0 or 1.

In another embodiment, the compounds are represented by Formula III, shown below:

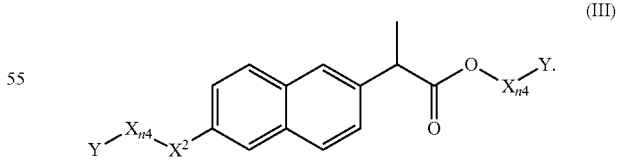

(III)

$X^2$ is O or —C(O)—O—.

X, Y, $R^2$, n1, n2, and n4 are as described above.

Some of the compounds of the invention may be referred to as hydrogen sulfide-releasing phospho-NSAIDs (POSH-NSAIDs), nitric oxide-releasing phospho-NSAIDs (PONO-NSAIDs), nitric oxide-hydrogen sulfide-releasing phospho-NSAIDs (PO-NOSH-NSAIDs).

Specific examples of compounds of the invention are shown below in Table 1.
TABLE 1
Structures of POSH-NSAIDs, PONO-NSAIDs, PO-NOSH-NSAIDS
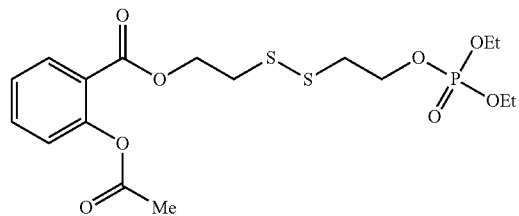 [SMILES: CCOP(=O)(OCC)OCCSSCCOC(=O)c1ccccc1OC(C)=O]
POSH-Aspirin
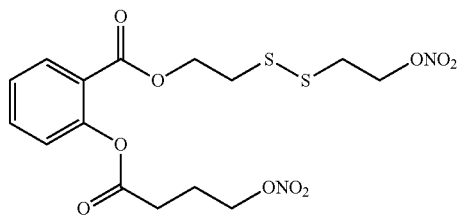
SSNO-Aspirin
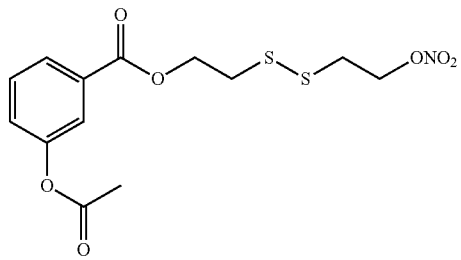
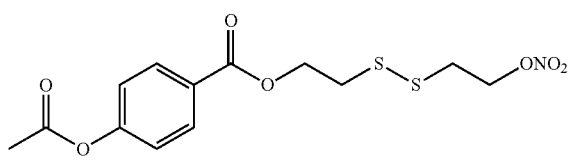
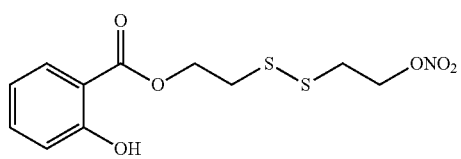
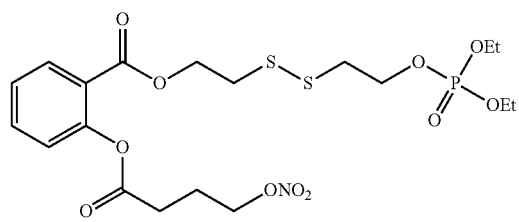
POSH-NO TABLE 1-continued
Structures of POSH-NSAIDs, PONO-NSAIDs, PO-NOSH-NSAIDS
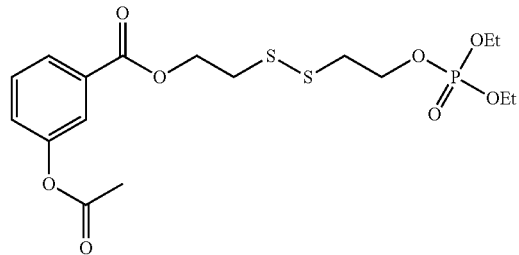 [SMILES: CCOP(=O)(OCC)OCCSSCCOC(=O)c1cccc(OC(C)=O)c1]
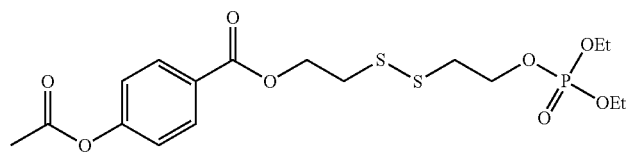 [SMILES: CCOP(=O)(OCC)OCCSSCCOC(=O)c1ccc(OC(C)=O)cc1]
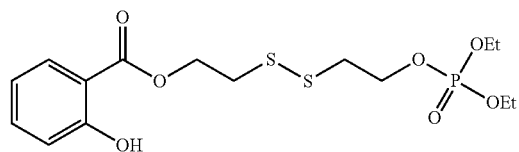 [SMILES: CCOP(=O)(OCC)OCCSSCCOC(=O)c1ccccc1O]
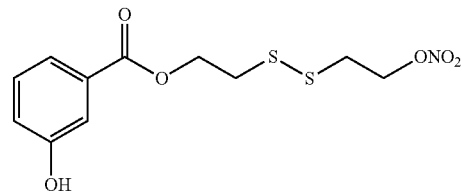
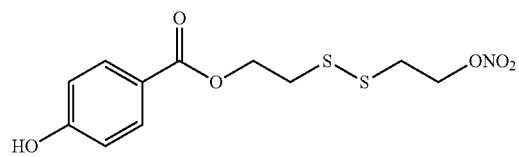
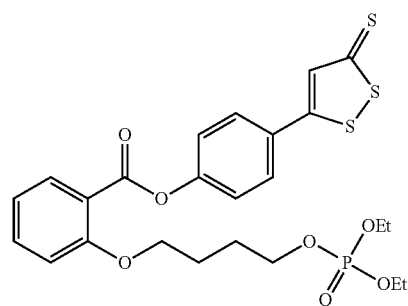 [SMILES: CCOP(=O)(OCC)OCCCCOc1ccccc1C(=O)Oc1ccc(-c2cc(=S)ss2)cc1]
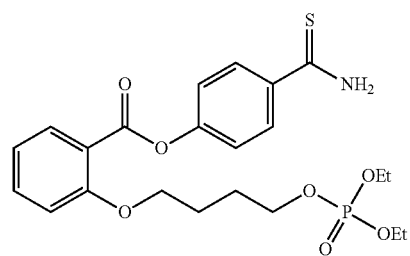 [SMILES: CCOP(=O)(OCC)OCCCCOc1ccccc1C(=O)Oc1ccc(C(N)=S)cc1]

TABLE 1-continued
Structures of POSH-NSAIDs, PONO-NSAIDs, PO-NOSH-NSAIDS
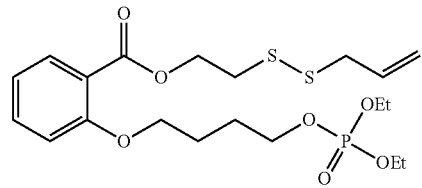 [SMILES: C=CCSSCCOC(=O)c1ccccc1OCCCCOP(=O)(OCC)OCC]
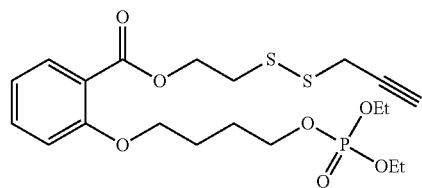 [SMILES: C#CCSSCCOC(=O)c1ccccc1OCCCCOP(=O)(OCC)OCC]
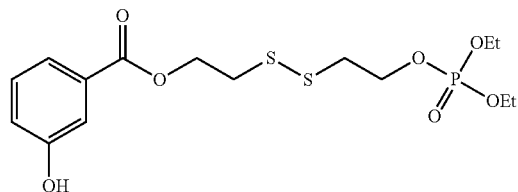 [SMILES: CCOP(=O)(OCC)OCCSSCCOC(=O)c1cccc(O)c1]
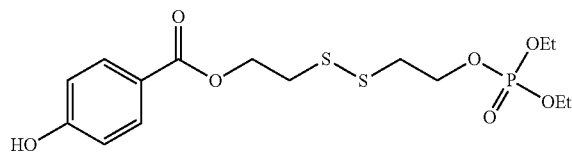 [SMILES: CCOP(=O)(OCC)OCCSSCCOC(=O)c1ccc(O)cc1]
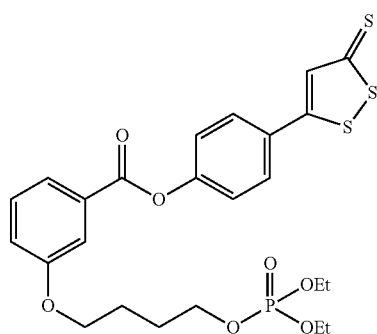 [SMILES: CCOP(=O)(OCC)OCCCCOc1cccc(C(=O)Oc2ccc(-c3cc(=S)ss3)cc2)c1]
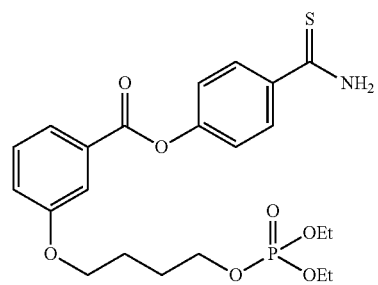 [SMILES: CCOP(=O)(OCC)OCCCCOc1cccc(C(=O)Oc2ccc(C(N)=S)cc2)c1]

TABLE 1-continued
Structures of POSH-NSAIDs, PONO-NSAIDs, PO-NOSH-NSAIDS
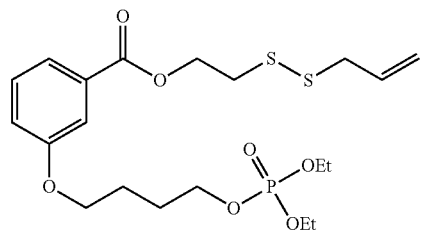 [SMILES: C=CCSSCCOC(=O)c1cccc(OCCCCOP(=O)(OCC)OCC)c1]
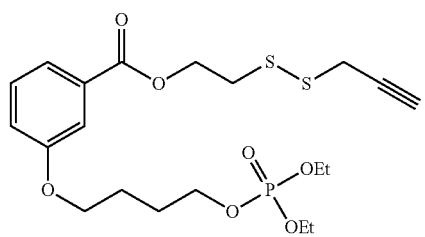 [SMILES: C#CCSSCCOC(=O)c1cccc(OCCCCOP(=O)(OCC)OCC)c1]
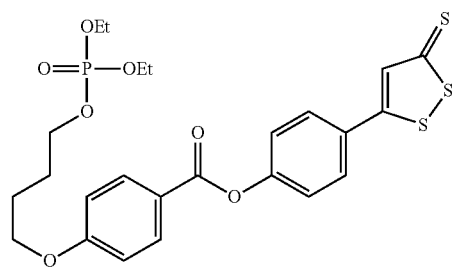 [SMILES: CCOP(=O)(OCC)OCCCCOc1ccc(C(=O)Oc2ccc(-c3cc(=S)ss3)cc2)cc1]
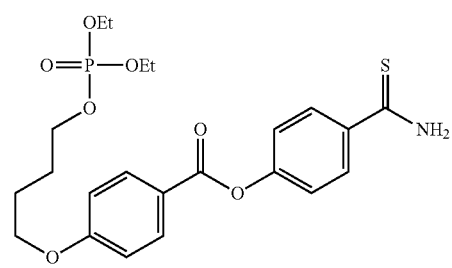 [SMILES: CCOP(=O)(OCC)OCCCCOc1ccc(C(=O)Oc2ccc(C(N)=S)cc2)cc1]
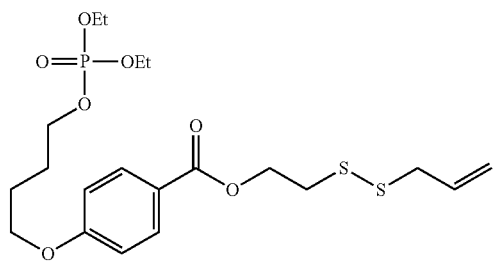 [SMILES: C=CCSSCCOC(=O)c1ccc(OCCCCOP(=O)(OCC)OCC)cc1]
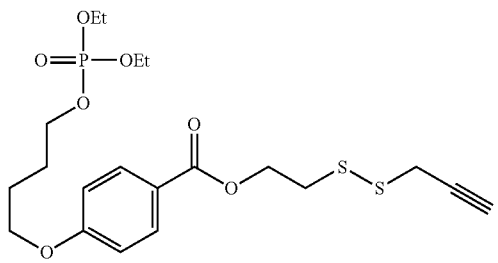 [SMILES: C#CCSSCCOC(=O)c1ccc(OCCCCOP(=O)(OCC)OCC)cc1]

TABLE 1-continued
Structures of POSH-NSAIDs, PONO-NSAIDs, PO-NOSH-NSAIDS
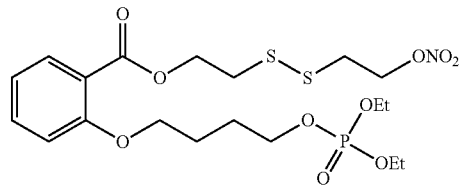
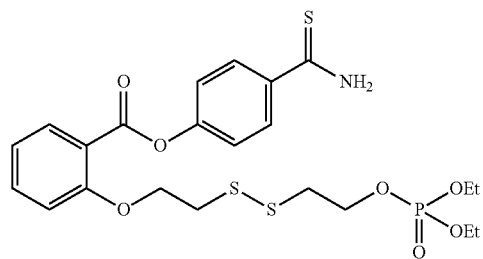 [SMILES: CCOP(=O)(OCC)OCCSSCCOc1ccccc1C(=O)Oc1ccc(C(N)=S)cc1]
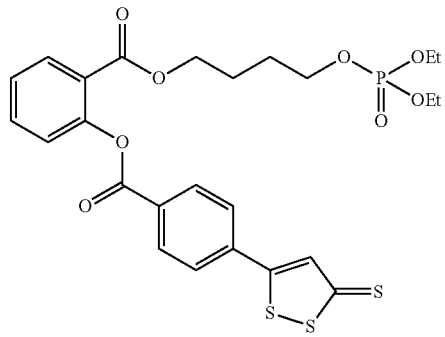 [SMILES: CCOP(=O)(OCC)OCCCCOC(=O)c1ccccc1OC(=O)c1ccc(-c2cc(=S)ss2)cc1]
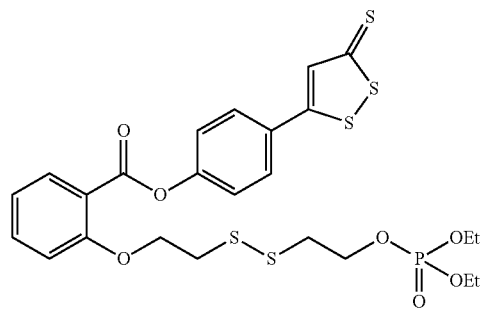 [SMILES: CCOP(=O)(OCC)OCCSSCCOc1ccccc1C(=O)Oc1ccc(-c2cc(=S)ss2)cc1]
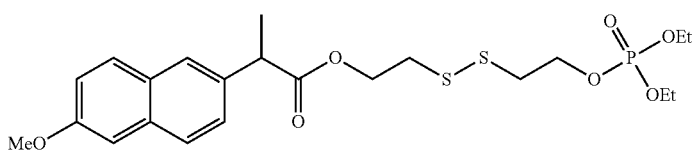 [SMILES: CCOP(=O)(OCC)OCCSSCCOC(=O)C(C)c1ccc2cc(OC)ccc2c1]
POSH-Napro
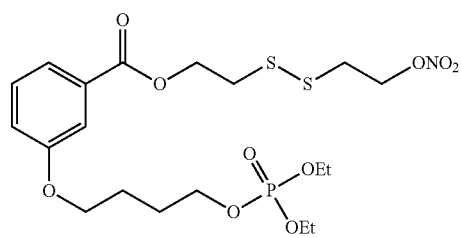

TABLE 1-continued
Structures of POSH-NSAIDs, PONO-NSAIDs, PO-NOSH-NSAIDS
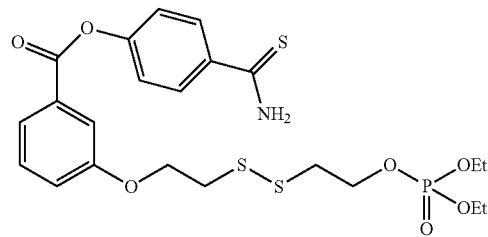 [SMILES: CCOP(=O)(OCC)OCCSSCCOc1cccc(C(=O)Oc2ccc(C(N)=S)cc2)c1]
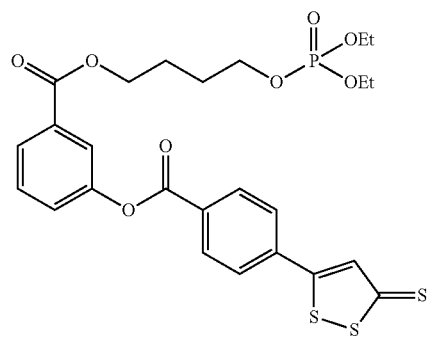 [SMILES: CCOP(=O)(OCC)OCCCCOC(=O)c1cccc(OC(=O)c2ccc(-c3cc(=S)ss3)cc2)c1]
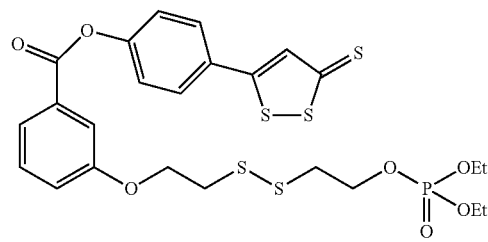 [SMILES: CCOP(=O)(OCC)OCCSSCCOc1cccc(C(=O)Oc2ccc(-c3cc(=S)ss3)cc2)c1]
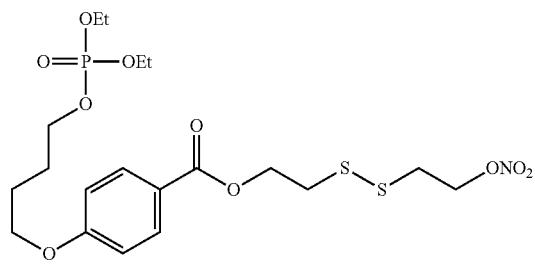
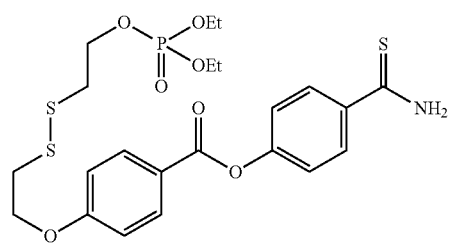 [SMILES: CCOP(=O)(OCC)OCCSSCCOc1ccc(C(=O)Oc2ccc(C(N)=S)cc2)cc1]

TABLE 1-continued
Structures of POSH-NSAIDs, PONO-NSAIDs, PO-NOSH-NSAIDS
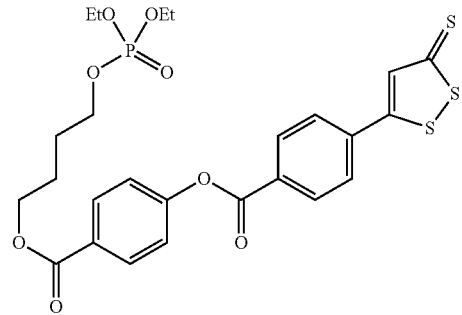 [SMILES: CCOP(=O)(OCC)OCCCCOC(=O)c1ccc(OC(=O)c2ccc(-c3cc(=S)ss3)cc2)cc1]
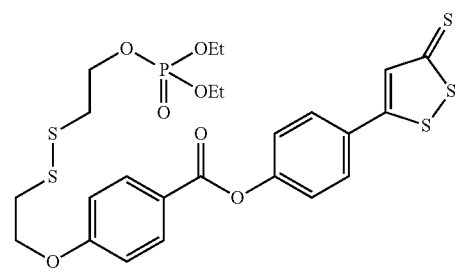 [SMILES: CCOP(=O)(OCC)OCCSSCCOc1ccc(C(=O)Oc2ccc(-c3cc(=S)ss3)cc2)cc1]
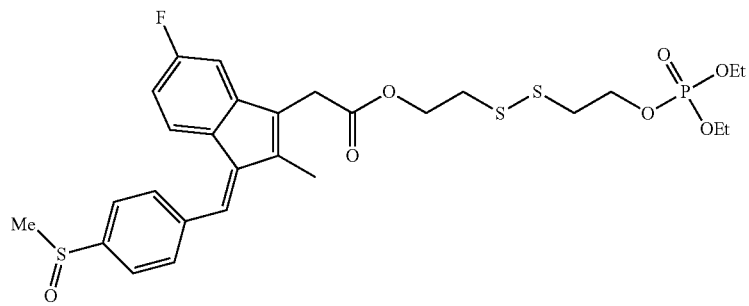 [SMILES: CCOP(=O)(OCC)OCCSSCCOC(=O)CC1=C(C)/C(=C/c2ccc(S(C)=O)cc2)c2ccc(F)cc21]
POSH-Sulindac
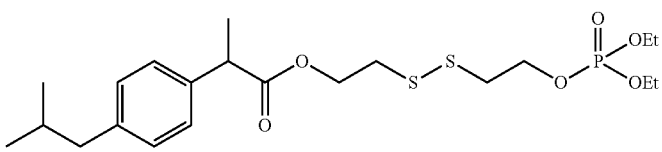 [SMILES: CCOP(=O)(OCC)OCCSSCCOC(=O)C(C)c1ccc(CC(C)C)cc1]
PHOS-Ibuprofen
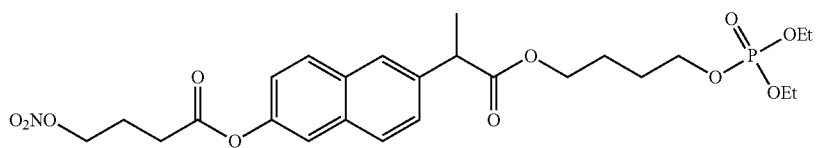
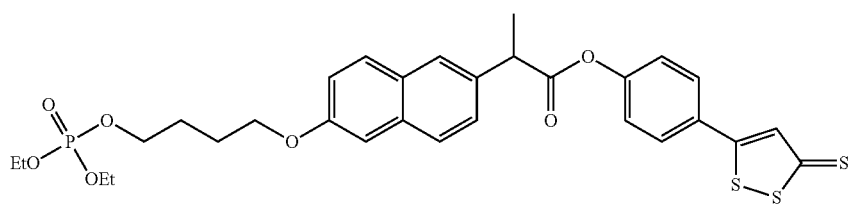 [SMILES: CCOP(=O)(OCC)OCCCCOc1ccc2cc(C(C)C(=O)Oc3ccc(-c4cc(=S)ss4)cc3)ccc2c1]

TABLE 1-continued
Structures of POSH-NSAIDs, PONO-NSAIDs, PO-NOSH-NSAIDS
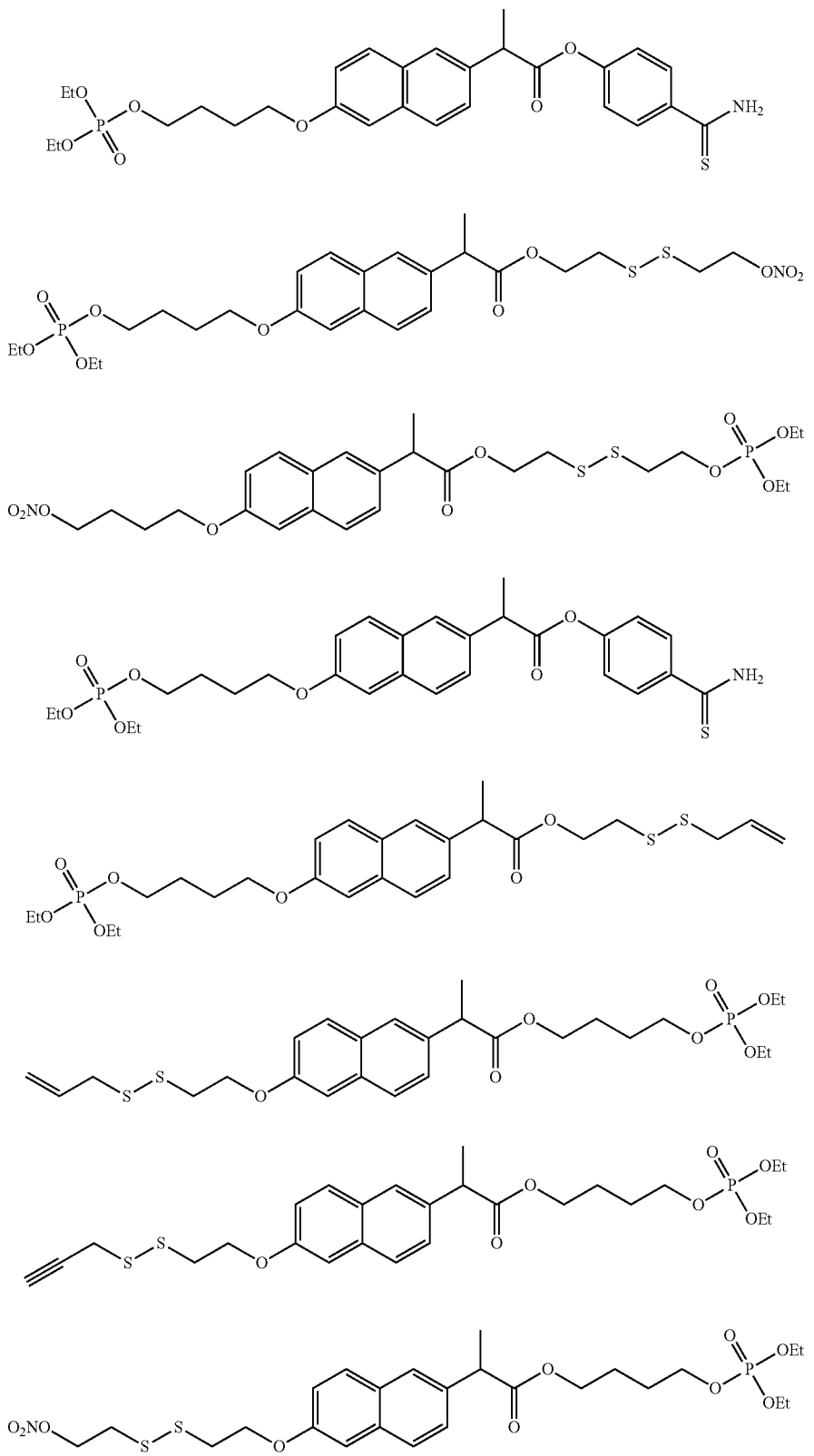

TABLE 1-continued
Structures of POSH-NSAIDs, PONO-NSAIDs, PO-NOSH-NSAIDS
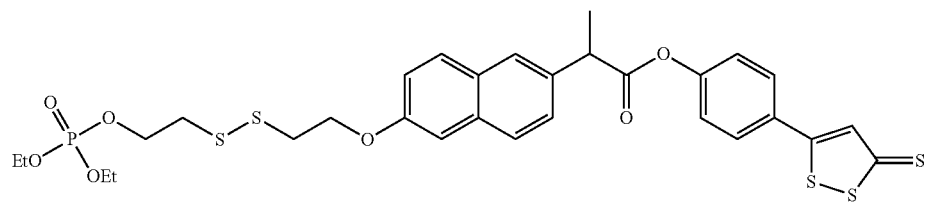 [SMILES: CCOP(=O)(OCC)OCCSSCCOc1ccc2cc(C(C)C(=O)Oc3ccc(-c4cc(=S)ss4)cc3)ccc2c1]
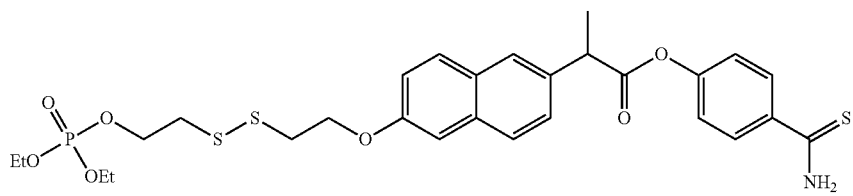 [SMILES: CCOP(=O)(OCC)OCCSSCCOc1ccc2cc(C(C)C(=O)Oc3ccc(C(N)=S)cc3)ccc2c1]
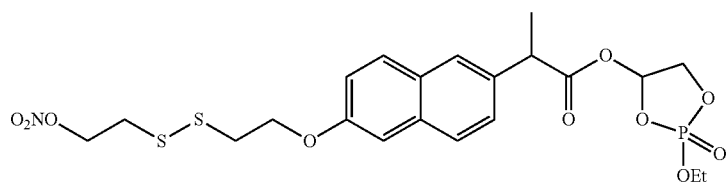
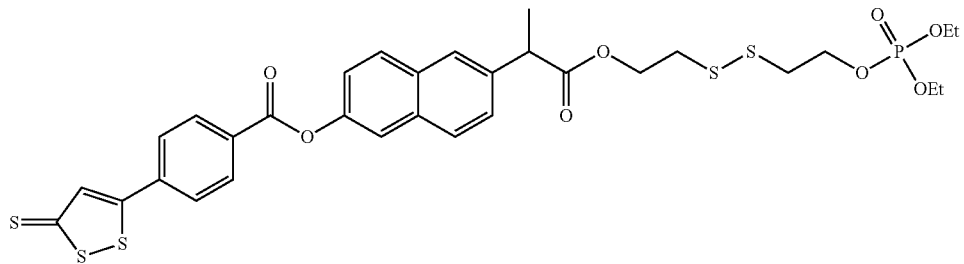 [SMILES: CCOP(=O)(OCC)OCCSSCCOC(=O)C(C)c1ccc2cc(OC(=O)c3ccc(-c4cc(=S)ss4)cc3)ccc2c1]
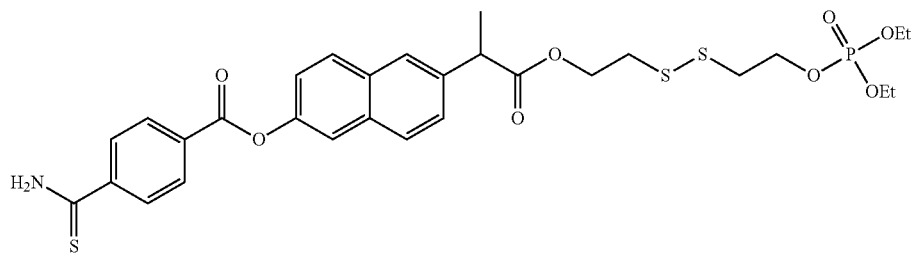 [SMILES: CCOP(=O)(OCC)OCCSSCCOC(=O)C(C)c1ccc2cc(OC(=O)c3ccc(C(N)=S)cc3)ccc2c1]
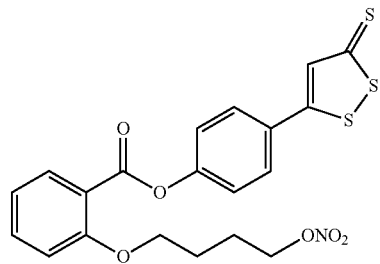

TABLE 1-continued

Structures of POSH-NSAIDs, PONO-NSAIDs, PO-NOSH-NSAIDS

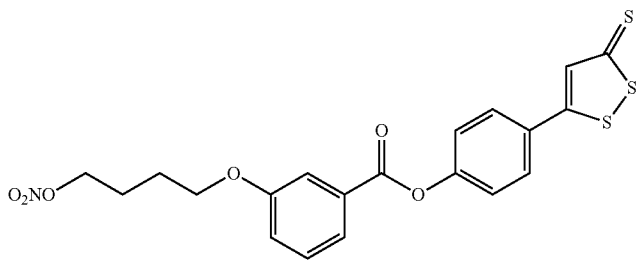

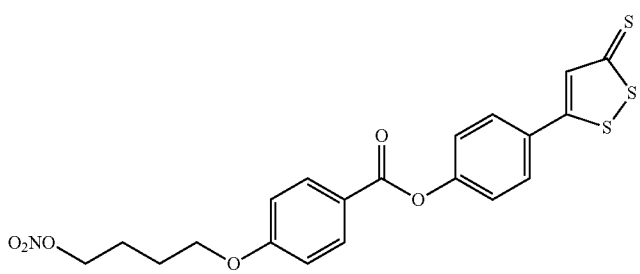

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. R, X, Y, etc). Each group contains multiple members. For example, Y independently represents —OP(O)(OEt)$_2$,

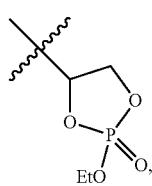

—OSO$_2$R$^2$, —OSO$_2$OR$^2$, —OB(OR$^2$)$_2$, halo, an H$_2$S releasing moiety, or an NO releasing moiety. Each member may be combined with each other member to form additional sub-groups, e.g., —OP(O)(OEt)$_2$, —OSO$_2$R$^2$, —OSO$_2$OR$^2$, and an NO releasing moiety; —OP(O)(OEt)$_2$, an H$_2$S releasing moiety, and an NO releasing moiety; and

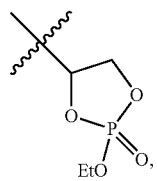

—OSO$_2$R$^2$, —OSO$_2$OR$^2$, and —OB(OR$^2$)$_2$.

The instant invention further contemplates embodiments in which each element listed under one group may be combined with each and every element listed under any other group. For example, R is identified above as representing an NSAID or R$^1$—C(O)—X$^1$—. X is identified above as being an alkyl, a cycloalkyl, an aryl, or —(CH$_2$)$_{n1}$—S$_{n2}$—(CH$_2$)$_{n1}$—. Each element of R (an NSAID or R$^1$—C(O)—X$^1$—) can be combined with each and every element of X (an alkyl, a cycloalkyl, an aryl, or —(CH$_2$)$_{n1}$—S$_{n2}$—(CH$_2$)$_{n1}$—). For example, in one embodiment, R may be an NSAID such as aspirin and X may be methyl. Alternatively, R may be R$^1$—C(O)—X$^1$—, and X may be phenyl, etc. Similarly, a third parameter is Y, in which the elements are defined as —OP(O)(OEt)$_2$,

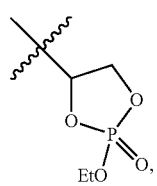

—OSO$_2$R$^2$, —OSO$_2$OR$^2$, —OB(OR$^2$)$_2$, halo, an H$_2$S releasing moiety, or an NO releasing moiety. Each of the above embodiments may be combined with each and every element of R and X. For example, in the embodiment wherein R is an NSAID such as ibuprofen and X is —(CH$_2$)$_2$—S—S—(CH$_2$)$_2$—, Y may be —OP(O)(OEt)$_2$ (or any other chemical moiety within the element of Y).

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Pharmaceutically Acceptable Salts

The present invention also relates to pharmaceutically acceptable salts of the NSAID derivatives. Pharmaceutically acceptable salts include pharmaceutically acceptable acid addition salts, pharmaceutically acceptable metal salts, ammonium and alkylated ammonium salts. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

The pharmaceutically acceptable salts of the NSAID derivatives of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Prodrugs

The invention also encompasses prodrugs of the present compounds, which on administration undergo chemical conversion by metabolic processes before becoming pharmacologically active substances. In general, such prodrugs will be functional derivatives of the compounds of the compounds described herein, which are readily convertible in vivo into the required compound. Conventional procedures for the selection and preparation of suitable prodrug derivatives are described, for example, in "Design of Prodrugs", ed. H. Bundgaard, Elsevier, 1985.

Synthesis of the Derivatives

The compounds of the invention may be synthesized by methods well known in the art. For example, the POSH-NSAID compounds may be synthesized by treating an NSAID containing a carboxylic acid (a) with 2-hydroxyethyl disulfide in the presence of DCC/DMAP in DCM undergo mono esterification. The product is reacted with (b) diethyl chlorophosphate in the presence of triethyl amine and DMAP to yield the desired POSH-NSAID. See Scheme 1, below.

Scheme 1. Preparation of POSH-NSAID Compounds

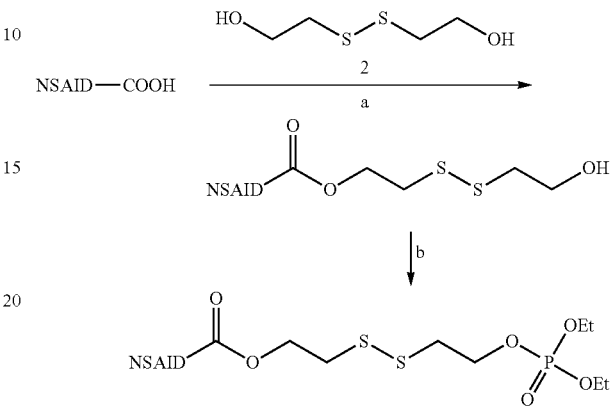

a. DCC/DMAP in DCM at 0° C. - rt, 12 h.; b. Diethylchlorophosphate, Et$_3$N, DMAP, EtOAc, rt, 6 h Uses of the Derivatives The invention also relates to a method of treating an inflammatory disease in a subject in need thereof. The method comprises administering to the subject the compound of Formula I, II, or III or a pharmaceutically acceptable salt thereof. The inflammatory disease may be cancer, rheumatoid arthritis, intestine inflammation, stomach ulcer, a cardiovascular disease, or a neurodegenerative disease.

The method and compounds of the invention may be employed alone, or in combination with other anti-inflammatory agents. The combination of these anti-inflammatory agents and the compounds of the invention will provide new agents for the treatment of cancer, rheumatoid arthritis, intestine inflammation, stomach ulcer, a cardiovascular disease, and neurodegenerative disease.

The invention also relates to a pharmaceutical composition including an effective amount of a compound according to Formulas I, II, or III or a pharmaceutically acceptable salt thereof, and a pharmaceutically acceptable carrier.

An effective amount of a compound of Formula I, II, or III or a pharmaceutically acceptable salt thereof as used herein is any amount effective to treat a patient afflicted with an inflammatory disease. Modes of administration and doses can be determined by those having skill in the art. An effective amount of the compound will vary with the group of patients (age, sex, weight, etc.), the nature and severity of the condition to be treated, the particular compound administered, and its route of administration. Amounts suitable for administration to humans are routinely determined by physicians and clinicians during clinical trials.

The minimum dose of the compound is the lowest dose at which efficacy is observed. For example, the minimum dose of the compound may be about 0.1 mg/kg/day, about 1 mg/kg/day, or about 3 mg/kg/day.

The maximum dose of the compound is the highest dose at which efficacy is observed in a patient, and side effects are tolerable. For example, the maximum dose of the compound may be about 10 mg/kg/day, about 9 mg/kg/day, or about 8 mg/kg/day. In another embodiment, the maximum dose of the compound may be up to about 50 mg/kg/day.

A derivative useful in the methods of the present invention may be administered by any method known in the art. Some examples of suitable modes of administration include oral and systemic administration. Systemic administration can be enteral or parenteral. Liquid or solid (e.g., tablets, gelatin capsules) formulations can be employed.

Parenteral administration of the NSAID derivatives include, for example intravenous, intramuscular, and subcutaneous injections. For instance, a chemical compound may be administered to a patient by sustained release, as is known in the art. Sustained release administration is a method of drug delivery to achieve a certain level of the drug over a particular period of time.

Other routes of administration include oral, topical, intrabronchial, and intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a chemical compound can be accomplished by a nebulizer or liquid mist.

The chemical compound can be formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The chemical compound can be formulated into a composition containing one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the chemical compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v). Other preferred surfactants include Solutol H-15 and Cremophore EL.

The salt or buffering agent may be any salt or buffering agent, such as for example sodium chloride, or sodium/potassium phosphate, respectively. Preferably, the buffering agent maintains the pH of the chemical compound formulation in the range of about 5.5 to about 7.5. The salt and/or buffering agent is also useful to maintain the osmolality at a level suitable for administration to a patient. Preferably the salt or buffering agent is present at a roughly isotonic concentration of about 150 mM to about 300 mM.

The chemical compound can be formulated into a composition which may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as, for example a morphine derivative; or an isotonic agent etc. As a further precaution against oxidation or other spoilage, the composition may be stored under nitrogen gas in vials sealed with impermeable stoppers.

EXAMPLES

Example 1

Synthesis of POSH-Aspirin

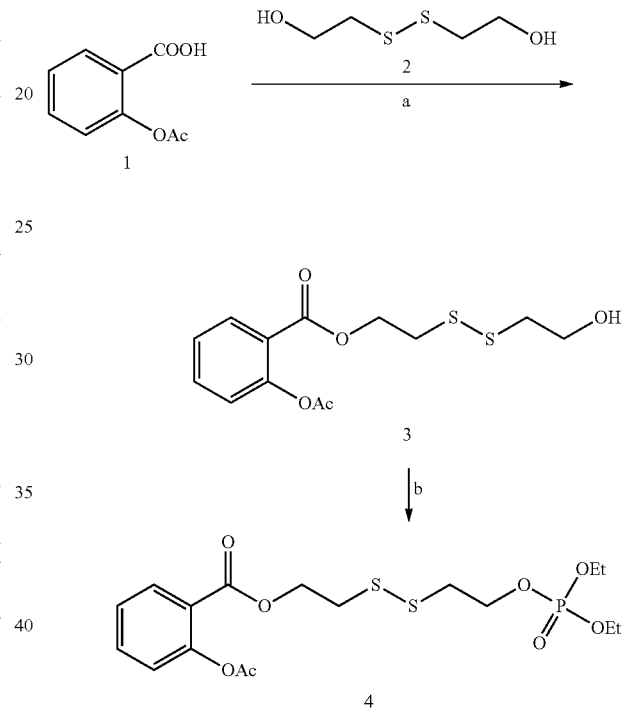

a. DCC/DMAP in DCM at 0° C. - rt, 12 h.; b. Diethylchlorophosphate, Et$_3$N, DMAP, EtOAc, rt, 6 h Aspirin treated (1) with 2-hydroxyethyl disulfide (2) in the presence of DCC/DMAP in DCM undergoes mono esterification to yield compound 3. Compound 3 is further treated with diethyl chlorophosphate in the presence of triethyl amine and DMAP to yield the desired POSH-ASA (4).

Spectral Data for Compound 3

$^1$H-NMR (500 MHz, CDCl$_3$): δ 2.37 (s, 3H), 2.91 (t, 2H, J=6.5 Hz), 3.04 (t, 2H, J=6.5 Hz), 3.90 (t, 2H, J=7.2 Hz), 4.57 (t, 2H, J=7.2 Hz), 7.13 (d, 2H, J=8.2 Hz), 7.34 (d, 2H, J=7.2 Hz), 7.60 (2H, dt, J=7.2, 1.4 Hz), 8.04 (2H, J=8.2, 1.4 Hz). EIMS: 317 (M$^+$+1), 339 (M$^+$+Na).

Spectral Data for Compound 4

$^1$H-NMR (500 MHz, CDCl$_3$): δ 1.36 (m, 6H), 2.36 (s, 3H), 2.98 (t, 2H, J=6.8 Hz), 3.04 (t, 2H, J=6.8 Hz), 4.10 (m, 4H), 4.24 (t, 2H, J=7.2 Hz), 4.56 (t, 2H, J=7.2 Hz), 7.10 (d, 2H, J=8.2 Hz), 7.33 (t, 2H, J=7.2 Hz), 7.58 (2H, t, J=7.2), 8.02 (2H, J=8.2). EIMS: 453 (M$^+$+1), 475 (M$^+$+Na).

Example 2

Synthesis of POSH-Naproxen

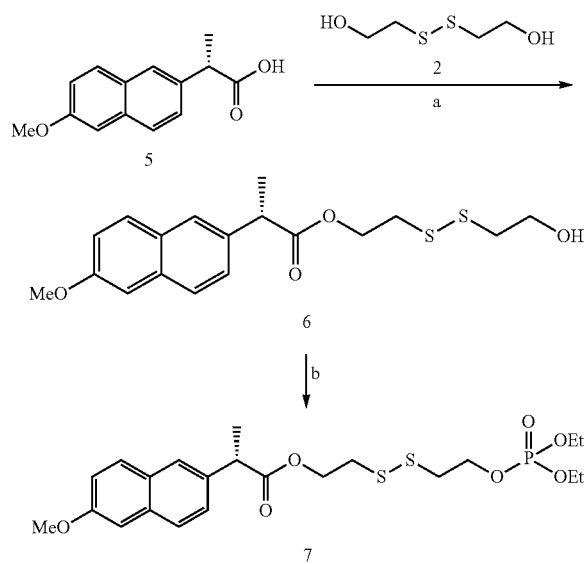

Naproxen treated (5) with 2-hydroxyethyl disulfide (2) in the presence of DCC/DMAP in DCM undergoes mono esterification to yield compound 6. Compound 6 is further treated with diethyl chlorophosphate in the presence of triethyl amine and DMAP to yield POSH-Naproxen (7).

Spectral Data for Compound 6

$^1$H-NMR (500 MHz, CDCl$_3$): δ 1.33 (t, 6H, J=7.0 Hz), 1.59 (d, 3H, J=7.32 Hz), 2.87 (m, 4H), 3.76 (t, 2H, J=6.6 Hz), 3.90 (s, 3H), 4.12 (m, 1H), 4.2-4.4 (m, 2H), 7.11 (m, 2H), 7.39 (m, 1H), 7.69 (m, 3H). EIMS: 367 (M$^+$+1), 389 (M$^+$+Na).

Spectral Data for Compound 7

$^1$H-NMR (500 MHz, CDCl$_3$): δ 1.57 (d, 3H, J=7.3 Hz), 2.77 (t, 2H, J=5.4 Hz), 2.87 (t, 2H, J=5.4 Hz), 3.87 (m, 1H), 3.91 (s, 3H), 4.11 (m, 4H), 4.20 (m, 2H), 4.34 (m, 2H), 7.13 (m, 2H), 7.40 (dd, 1H, J=8.31, 1.47 Hz), 7.66 (bs, 1H), 7.40 (d, 2H, J=8.31, 1.47 Hz), 7.70 (d, 2H, J=8.8 Hz). EIMS: 503 (M$^+$+1), 525 (M$^+$+Na).

Example 3

Synthesis of Compound 8 (4-(3-thioxo-3H-1,2-dithiol-5-yl)phenyl 2-(4-(nitrooxy) butoxy)benzoate)

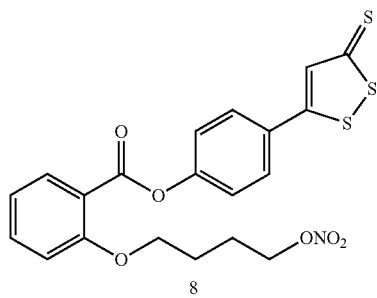

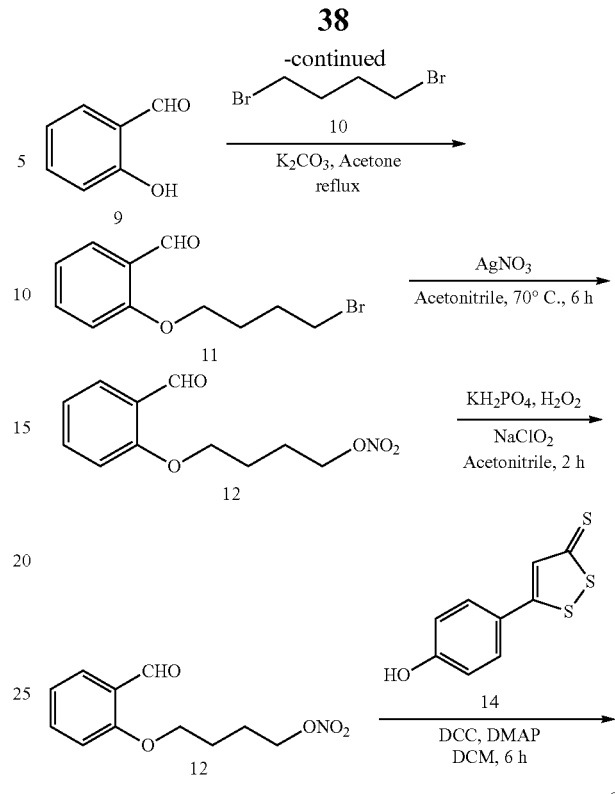

Synthetic Scheme for Compound 8

Synthesis of compound 11 (2-(4-bromobutoxy)benzaldehyde)

To the solution of salicyladehyde (9, 1.5 g, 12.29 mmol) in acetone was added K$_2$CO$_3$ (2.48 g, 18.04 mmol) and 1,4-dibromobutane (10, 2.65 g, 12.29 mmol). The whole reaction mixture was refluxed for 12 h, after completion of the reaction as checked by TLC, filtered off and concentrated under the reduced pressure to get the crude product. The obtained crude product was purified by silica gel column chromatography by eluting with 20% hexane/ethyl acetate to afford the pure compound 11 (yield, 2.05 g, 65%).

Synthesis of compound 12 (4-(2-formylphenoxy)butyl nitrate)

To the solution of bromo compound 11 (1.0 g, 3.9 mmol) in CH$_3$CN (80 mL) was added AgNO$_3$ (1.32 g, 7.8 mmol) and stirred at 70° C. for 6 h. The reaction mixture was filtered through Celite and concentrated under reduced pressure. The obtained crude residue was treated with CH$_2$Cl$_2$ (50 mL) and H$_2$O (50 mL). After separation, the aqueous layer was extracted twice with CH$_2$Cl$_2$ (50 mL). The combined organic layers were dried, filtered, and concentrated under reduced pressure. The crude product thus obtained was purified by silica gel column chromatography to get the nitro compound 12 with 68% yield (0.6 g).

$^1$H-NMR (CDCl3, 500 MHz): δ 2.0 (m, 4H), 4.16 (t, J=6.0 Hz, 2H), 4.53 (t, J=6.4 Hz, 2H), 7.04 (d, J=8.2 Hz, 1H), 7.1 (d, J=7.8 Hz, 1H), 7.38 (d, J=8.8 Hz, 2H), 7.45 (s, 1H), 7.59 (dt, J=8.8, 1.47 Hz, 1H), 7.63 (d, J=8.8 Hz, 2H), 8.06 (dd, J=7.3, 1.46 Hz, 1H).

ESIMS: m/z 464 (M$^+$+1).

Synthesis of compound 13
(2-(4-(nitrooxy)butoxy)benzoic acid)

To the solution of compound 12 (0.5 g, 2.09 mmol) in acetonitrile (30 mL) at 0° C. was added a solution of $KH_2PO_4$ (0.4 g, 2.94 mmol) in water (5 mL) and 30% $H_2O_2$ (0.25 mL, 2.19 mmol), then added drop wise a solution of 80% $NaClO_2$ (0.3 g, 2.65 mmol) in water (6.0 mL). The whole reaction mixture was stirred at same temperature for 2 h. The reaction was completed as monitored by TLC $Na_2SO_3$ was added to destroy the excess of $H_2O_2$. After acidification with 6M HCl, the mixture was diluted with $H_2O$ (100 mL) and extracted twice with DCM (50 mL). The organic layer was dried filtered and concentrated under reduced pressure. The obtained crude product was purified by silica gel column chromatography to yield corresponding acid product 13 with 75% yield (0.4 g).

Synthesis of Compound 8 (4-(3-thioxo-3H-1,2-dithiol-5-yl)phenyl 2-(4-(nitrooxy) butoxy)benzoate)

To the solution of 2-(4-(nitrooxy)butoxy)benzoic acid (200.0 mg, 0.78 mmol) in dichloromethane was added DCC (170.0.0 mg, 0.78 mmol), DMAP (9.6 mg, 0.08 mmol) at 0° C. under argon atmosphere. Then added ADT-OH ((5-(4-Hydroxyphenyl)-3H-1,2-dithiole-3-Thione, 14) (178.0 mg, 0.78 mmol) and the whole reaction mixture was stirred at room temperature for overnight. After completion of the reaction as checked by TLC, filtered off and water was added then extracted into dichloromethane (2×75 ml). Organic solvent was removed under reduced pressure to get the crude product. Further it was purified by column chromatography to afford pure orange solid (8, 4-(3-thioxo-3H-1, 2-dithiol-5-yl)phenyl 2-(4-(nitrooxy)butoxy)benzoate, 261.0 mg, 72% yield).

$^1$H-NMR (CDCl3, 500 MHz): δ 2.0 (m, 4H), 4.16 (t, J=6.0 Hz, 2H), 4.53 (t, J=6.4 Hz, 2H), 7.04 (d, J=8.2 Hz, 1H), 7.1 (d, J=7.8 Hz, 1H), 7.38 (d, J=8.8 Hz, 2H), 7.45 (s, 1H), 7.59 (dt, J=8.8, 1.47 Hz, 1H), 7.63 (d, J=8.8 Hz, 2H), 8.06 (dd, J=7.3, 1.46 Hz, 1H).

ESIMS: m/z 464 (M$^+$+1).

Example 4

Synthesis of Compound 15

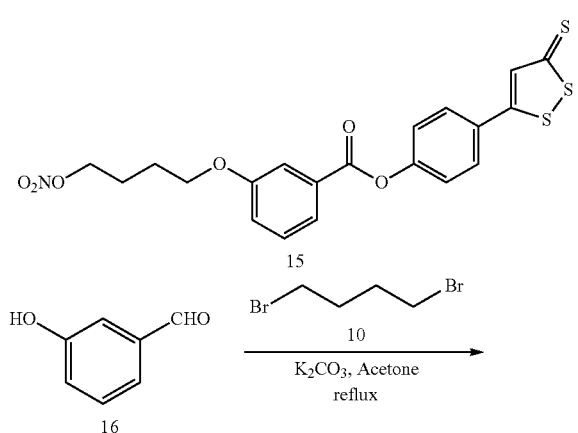

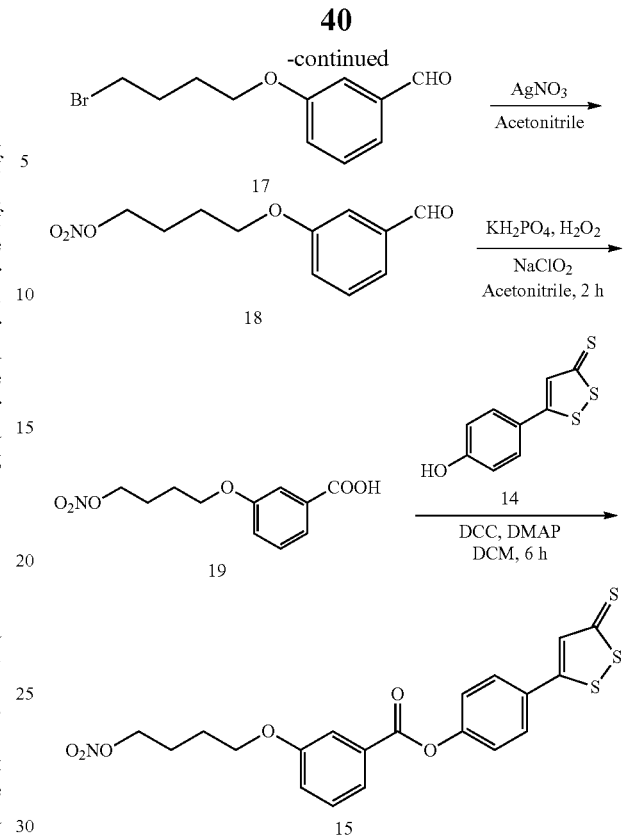

Synthetic Scheme for Compound 15

Synthesis of compound 17
(3-(4-bromobutoxy)benzaldehyde)

To the solution of meta salicyladehyde (16, 2.0 g, 16.38 mmol) in acetone was added $K_2CO_3$ (2.48 g, 18.04 mmol) and 1, 4-dibromobutane (10, 2.65 g, 16.38 mmol). The whole reaction mixture was refluxed for 18 h, after completion of the reaction as checked by TLC, filtered off and concentrated under the reduced pressure to get the crude product. The obtained crude product was purified by silica gel column chromatography by eluting with 20% hexane/ ethyl acetate to afford the pure compound 17 (yield, 1.98 g, 63%).

Synthesis of compound 18
(4-(3-formylphenoxy)butyl nitrate)

To the solution of bromo compound 17 (1.5 g, 5.85 mmol) in $CH_3CN$ (80 mL) was added $AgNO_3$ (1.98 g, 7.8 mmol) and stirred at 70° C. for 10 h. The reaction mixture was filtered through Celite and concentrated under reduced pressure. The obtained crude residue was treated with $CH_2Cl_2$ (60 mL) and $H_2O$ (60 mL). After separation, the aqueous layer was extracted twice with $CH_2Cl_2$ (50 mL). The combined organic layers were dried, filtered, and concentrated under reduced pressure. The crude product thus obtained was purified by silica gel column chromatography to get the nitro compound 18 with 68% yield (0.9 g).

Synthesis of compound 19
(3-(4-(nitrooxy)butoxy)benzoic acid)

To the solution of compound 18 (0.75 g, 3.13 mmol) in acetonitrile (50 mL) at 0° C. was added a solution of KH$_2$PO$_4$ (0.6 g, 4.41 mmol) in water (5 mL) and 30% H$_2$O$_2$ (0.375 mL, 3.28 mmol), then added drop wise a solution of 80% NaClO$_2$ (0.45 g, 3.97 mmol) in water (8.0 mL). The whole reaction mixture was stirred at same temperature for 2 h. The reaction was completed as monitored by TLC Na$_2$SO$_3$ was added to destroy the excess of H$_2$O$_2$. After acidification with 6M HCl, the mixture was diluted with H$_2$O (100 mL) and extracted twice with DCM (50 mL). The organic layer was dried filtered and concentrated under reduced pressure. The obtained crude product was purified by silica gel column chromatography to yield corresponding acid product 19 with 72% yield (0.575 g).

Synthesis of Compound 15 (4-(3-thioxo-3H-1,2-dithiol-5-yl)phenyl 3-(4-(nitrooxy) butoxy)benzoate)

To the solution of 3-(4-(nitrooxy)butoxy)benzoic acid (19, 250.0 mg, 0.97 mmol) in dichloromethane was added DCC (211.4 mg, 0.97 mmol), DMAP (10.2 mg, 0.09 mmol) at 0° C. under argon atmosphere. Then added ADT-OH ((5-(4-hydroxyphenyl)-3H-1,2-dithiole-3-Thione, 14) (178.0 mg, 0.78 mmol) and the whole reaction mixture was stirred at room temperature for overnight. After completion of the reaction as checked by TLC, filtered off and water was added then extracted into dichloromethane (2×75 ml). Organic solvent was removed under reduced pressure to get the crude product. Further it was purified by column chromatography to afford pure orange solid (15, 4-(3-thioxo-3H-1,2-dithiol-5-yl)phenyl 3-(4-(nitrooxy)butoxy)benzoate, 339.8 mg, 75% yield).

$^1$H-NMR (CDCl3, 500 MHz): δ 1.97 (m, 4H), 4.09 (t, J=5.37 Hz, 2H), 4.56 (t, J=5.37 Hz, 2H), 7.20 (dd, J=7.8, 1.47 Hz, 1H), 7.38 (d, J=8.8 Hz, 2H), 7.44 (t, J=7.82 Hz, 1H), 7.43 (s, 1H), 7.60 (bs, 1H), 7.75 (d, J=8.8 Hz, 2H), 7.82 (d, J=7.8 Hz, 1H).

ESIMS: m/z 464 (M$^+$+1).

Example 5

Synthesis of Compound 20

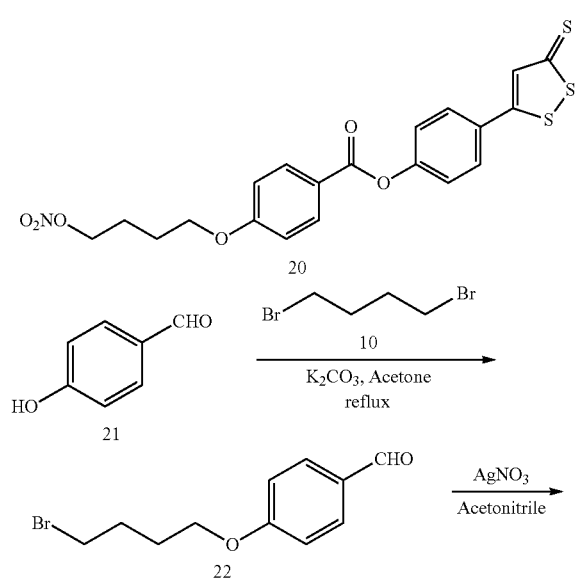

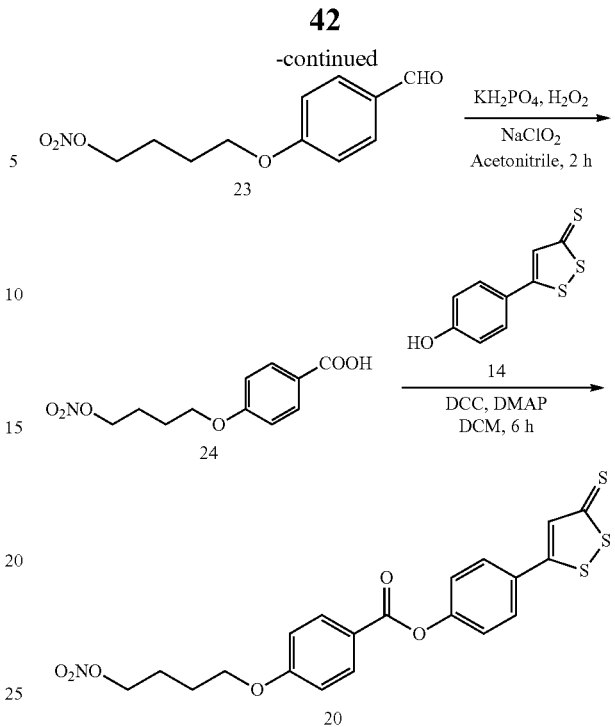

Synthetic Scheme for Compound 20

Synthesis of compound 22 (4-(4-bromobutoxy)benzaldehyde)

To the solution of para salicyladehyde (21, 1.25 g, 10.24 mmol) in acetone was added K$_2$CO$_3$ (2.06 g, 15.03 mmol) and 1, 4-dibromobutane (10, 2.20 g, 10.24 mmol). The whole reaction mixture was refluxed for 16 h, after completion of the reaction as checked by TLC, filtered off and concentrated under the reduced pressure to get the crude product. The obtained crude product was purified by silica gel column chromatography by eluting with 25% hexane/ethyl acetate to afford the pure compound 22 (yield, 1.78 g, 68%).

Synthesis of compound 23 (4-(4-formylphenoxy)butyl nitrate)

To the solution of bromo compound 22 (1.5 g, 5.85 mmol) in CH$_3$CN (80 mL) was added AgNO$_3$ (1.98 g, 7.8 mmol) and stirred at 70° C. for 10 h. The reaction mixture was filtered through Celite and concentrated under reduced pressure. The obtained crude residue was treated with CH$_2$Cl$_2$ (60 mL) and H$_2$O (60 mL). After separation, the aqueous layer was extracted twice with CH$_2$Cl$_2$ (50 mL). The combined organic layers were dried, filtered, and concentrated under reduced pressure. The crude product thus obtained was purified by silica gel column chromatography to get the nitro compound 23 with 65% yield (0.86 g).

Synthesis of compound 24 (4-(4-(nitrooxy)butoxy)benzoic acid)

To the solution of compound 23 (0.75 g, 3.13 mmol) in acetonitrile (50 mL) at 0° C. was added a solution of KH$_2$PO$_4$ (0.6 g, 4.42 mmol) in water (8 mL) and 30% H$_2$O$_2$ (0.38 mL, 3.28 mmol), then added drop wise a solution of 80% $NaClO_2$ (0.45 g, 3.97 mmol) in water (8.0 mL). The whole reaction mixture was stirred at same temperature for 2 h. The reaction was completed as monitored by TLC $Na_2SO_3$ was added to destroy the excess of $H_2O_2$. After acidification with 6M HCl, the mixture was diluted with $H_2O$ (100 mL) and extracted twice with DCM (50 mL). The organic layer was dried filtered and concentrated under reduced pressure. The obtained crude product was purified by silica gel column chromatography to yield corresponding acid product 24 with 68% yield (0.54 g).

Synthesis of Compound 20 (4-(3-thioxo-3H-1,2-dithiol-5-yl)phenyl 2-(4-(nitrooxy)butoxy)benzoate)

To the solution of 4-(4-(nitrooxy)butoxy)benzoic acid (225.0 mg, 0.87 mmol) in dichloromethane was added DCC (190.0 mg, 0.87 mmol), DMAP (11.0 mg, 0.09 mmol) at 0° C. under argon atmosphere. Then added ADT-OH ((5-(4-hydroxyphenyl)-3H-1,2-dithiole-3-Thione 14 (198.5 mg, 0.87 mmol) and the whole reaction mixture was stirred at room temperature for overnight. After completion of the reaction as checked by TLC, filtered off and water was added then extracted into dichloromethane (2×60 ml). Organic solvent was removed under reduced pressure to get the crude product. Further it was purified by column chromatography to afford pure orange solid (20, 4-(3-thioxo-3H-1,2-dithiol-5-yl)phenyl 2-(4-(nitrooxy)butoxy)benzoate, 262.0 mg, 68% yield).

$^1$H-NMR (CDCl3, 500 MHz): δ 1.97 (m, 4H), 4.10 (t, J=5.38 Hz, 2H), 4.57 (t, J=6.4 Hz, 2H), 6.99 (d, J=8.8 Hz, 2H), 7.37 (d, J=8.8 Hz, 2H), 7.44 (s, 1H), 7.74 (d, J=8.8 Hz, 2H), 8.16 (d, J=8.8 Hz, 2H).

ESIMS: m/z 464 ($M^+$+1).

Example 6

In Vitro Assays

Materials and Methods

Cell Culture: HT-29, SW-480 and HCT-15 human colon adenocarcinoma, MIA PaCa-2 and BxPC-3 human pancreatic cancer, LNCAP human prostate cancer, A549 human lung cancer, MCF-7 (estrogen receptor positive), MDA-MB 231 and SK-BR-3 (estrogen receptor negative) human breast cancer, and Jurkats human leukemia cell lines were obtained from American Type Tissue Collection (Manassas, Va.). All cells lines were grown as monolayers except for the Jurkats which were grown in suspension. The pancreatic and breast cancer cells were grown in Dulbecco's modified Eagle's medium, the prostate, Jurkat, SW-480 and HCT-15 colon cells were grown in RPMI 1640 medium, the lung cells were grown in F-12 and the colon HT-29 cells were grown in McCoy 5A. All media were supplemented with 10% fetal calf serum (Invitrogen, Carlsbad, Calif.) penicillin (50 U/ml), and streptomycin (50 μg/ml) (Invitrogen, Carlsbad, Calif.). Cells were seeded on culture dishes at a density of $25 \times 10^3$ cells/$cm^2$ and incubated at 37° C. in 5% $CO_2$ and 90% relative humidity. Single cell suspensions were obtained by trypsinization (0.05% trypsin/EDTA), and cells were counted using a hemocytometer. Viability was determined by the trypan blue dye exclusion method.

MTT Assay: Cell growth inhibitory effect of POSH compounds were measured using a colorimetric MTT assay kit (Roche, Indianapolis, Ind.). Cancer cells were plated in 96-well plates at a density of 50,000 cells/well. The cells were incubated for 24 h with different concentrations of POSH compounds. After the indicated time, 10 μl of MTT dye (3-[4,5-dimethylthiazol-2-yl]-2,5-diphenyl tetrazolium bromide, 5 mg/ml in phosphate buffered saline), was added to each well, and the plates were incubated for 2 hours at 37° C. Then, the media was aspirated, and add 100 μl of the solubilization solution (10% SDS in 0.01 M HCl) was added to each well to solubilize the formant crystals. The absorbance of the plates was measured on an ELISA reader at a wavelength of 570 nm. Each sample was performed in triplicate, and the entire experiment was repeated three times.

Results

As shown in Table 2, both POSH compounds (i.e., POSH-aspirin (POSH-ASA) and POSH-naproxen (POSH-NAP)) exhibited efficacy in inhibiting cell growth of the tested cancer cell lines and enhanced potency compared to aspirin and naproxen, respectively. POSH-ASA exhibited greater potency than POSH-NAP.

TABLE 2

$IC_{50}$ (μM) values at 24 h for cell growth inhibition in different cancer cell lines

| Agent | Colon | | | Breast | | | Pancreas | | Lung | Prostate | Leukemia |
| | HT-29 | HCT 15 | SW480 | MDA MB 231 | SKBR3 | MCF-7 | MIAPa Ca2 | BxPC3 | A549 | LNCAP | Jurkat |
|---|---|---|---|---|---|---|---|---|---|---|---|
| ASA | >5000 in all cell lines | | | | | | | | | | |
| POSH-ASA | 0.082 ± 0.006 | 0.075 ± 0.004 | 0.092 ± 0.005 | 0.180 ± 0.007 | 0.098 ± 0.004 | 0.242 ± 0.018 | 0.082 ± 0.008 | 0.075 ± 0.005 | 0.083 ± 0.008 | 0.075 ± 0.005 | 0.22 ± 0.007 |
| Enhanced Potency | >60,000 | >65,000 | >50,000 | >25,000 | >50,000 | >20,000 | >60,000 | >65,000 | >60,000 | >65,000 | >20,000 |
| NAP | 2800 ± 165 | 2950 ± 215 | 3110 ± 185 | 2900 ± 225 | 2890 ± 147 | 2100 ± 200 | 3200 ± 195 | 2600 ± 85 | 2650 ± 110 | 2990 ± 175 | 2385 ± 177 |
| POSH-NAP | 0.15 ± 0.01 | 0.12 ± 0.008 | 0.18 ± 0.007 | 0.15 ± 0.01 | 0.13 ± 0.007 | 0.19 ± 0.008 | 0.088 ± 0.009 | 0.10 ± 0.02 | 0.16 ± 0.01 | 0.13 ± 0.02 | 0.17 ± 0.01 |
| Enhanced Potency | ~18,000 | ~24,000 | ~17,000 | ~19,000 | ~22,000 | ~11,000 | ~36,000 | ~26,000 | ~16,000 | ~25,000 | ~14,000 |

Colon, breast, pancreas, lung, prostate, and leukemia cancer cell lines were treated with various concentrations of POSH-aspirin (POSH-ASA), or POSH-naproxen (POSH-NAP) and their traditional counterparts. Cell numbers were determined at 24 h from which $IC_{50}$ values were calculated. The ratios of NSAID/POSH-NSAID represent fold-enhancement in potency of the POSH-NSAID over the parent compound. Results are mean ± SEM of three independent determinations. In all cell lines and for all POSH-NSAIDs $P < 0.001$ compared to the respective parent NSAID.

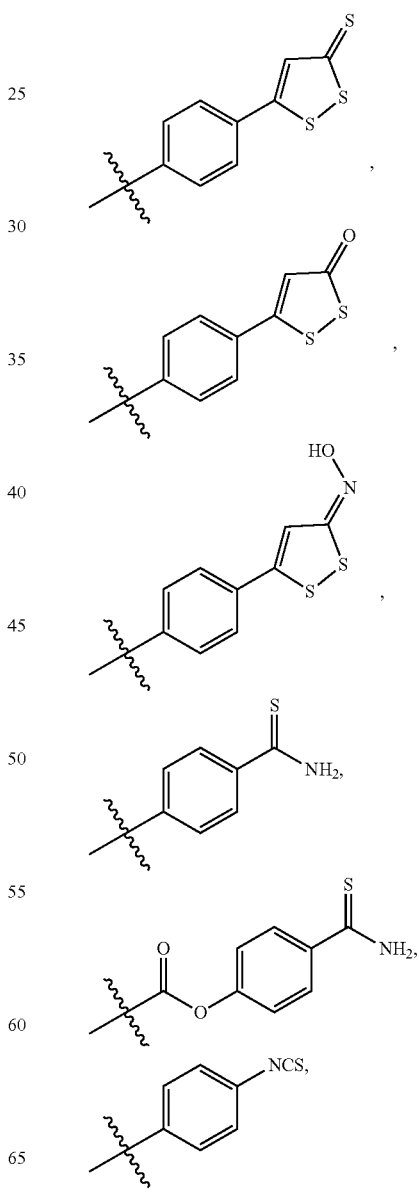

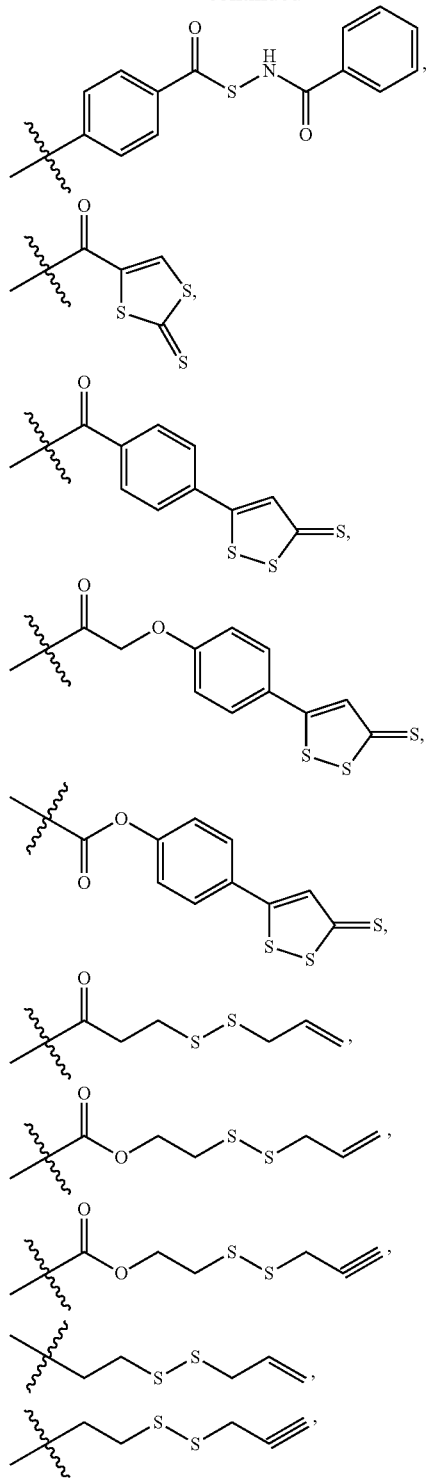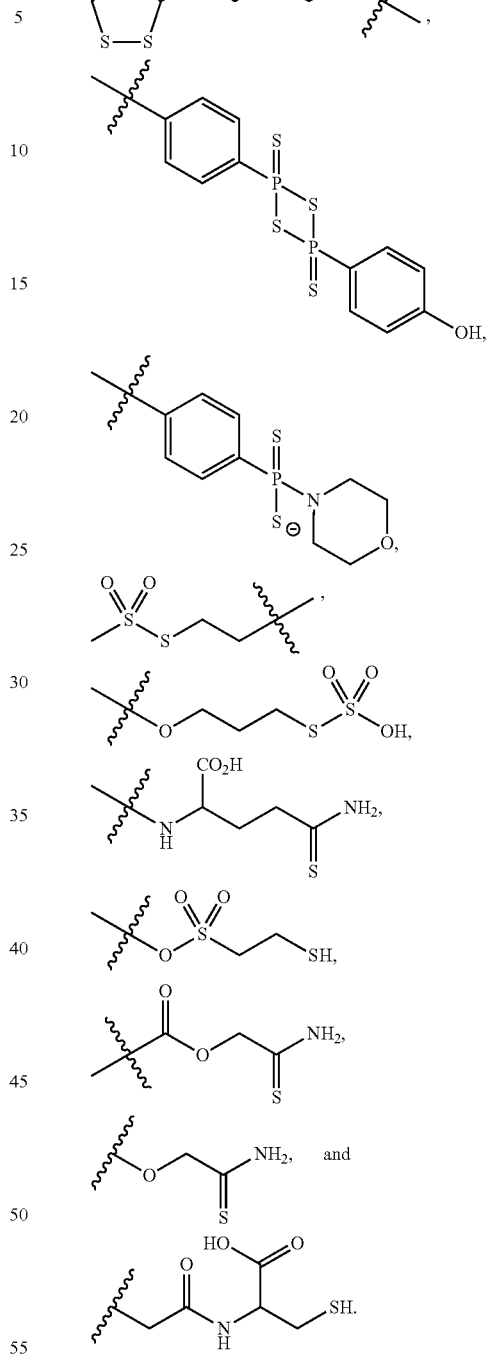

The invention claimed is:
1. A compound of Formula I:

R—X—Y  (I)

wherein:
R is aspirin;
X is a cycloalkyl, an aryl, or —(CH$_2$)$_{n1}$—S$_{n2}$—(CH$_2$)$_{n1}$—;
n1 is independently an integer from 1 to 20;
n2 is 2, 3, or 4;
Y is independently —OP(O)(OEt)$_2$,

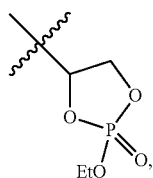

—OSO$_2$R$^2$, —OSO$_2$OR$^2$, —OB(OR$^2$)$_2$, or an H$_2$S releasing moiety;
R$^2$ is independently [—(CH$_2$)$_{n1}$—H];
cycloalkyl groups are carbocyclic or heterocyclic, fused or unfused, non-aromatic ring systems having a total of 3-16 ring members including substituent rings;
cycloalkyl groups may be unsubstituted or substituted with one or more substituent at any position;
aryl groups are carbocyclic or heterocyclic;
aryl groups may be unsubstituted or substituted with one or more substituent at any position;
cycloalkyl substituents are halo, hydroxyl, OR$^3$, SR$^3$, NH$_2$, NHR$^3$, alkyl, cycloalkyl, or aryl;
aryl substituents are halo, hydroxyl, OR$^3$, SR$^3$, NH$_2$, NHR$^3$, alkyl, cycloalkyl, aryl, nitro, carboxyl, or —O—C(O)-alkyl;
heterocyclic cycloalkyl and aryl groups have at least one heteroatom selected from oxygen, nitrogen, and sulfur;
R$^3$ represents alkyl, cycloalkyl, aryl, or halo;
alkyl groups are branched or unbranched, saturated or unsaturated, and have 1-20 carbon atoms in their longest chain; and
halo substituents are fluoro, chloro, or bromo.

2. A compound according to claim 1, wherein the H$_2$S releasing moiety is selected from the group consisting of

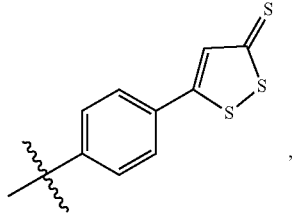

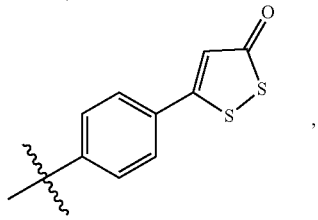

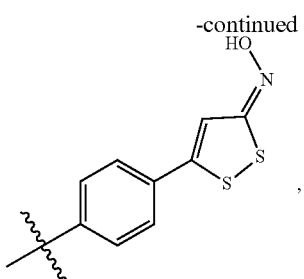

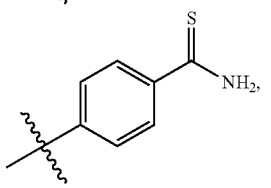

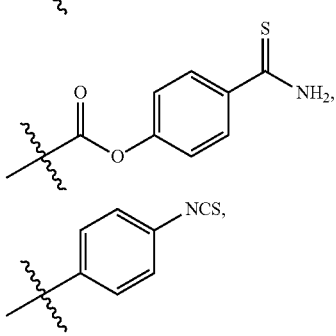

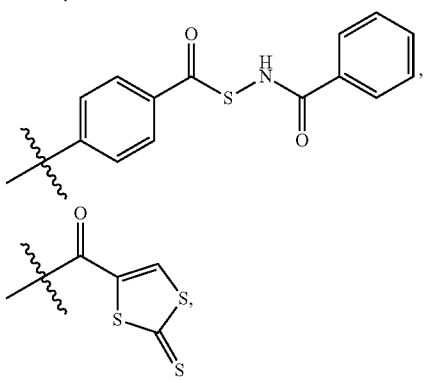

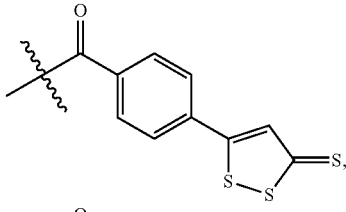

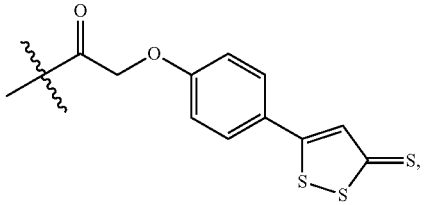

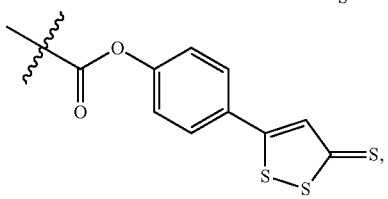

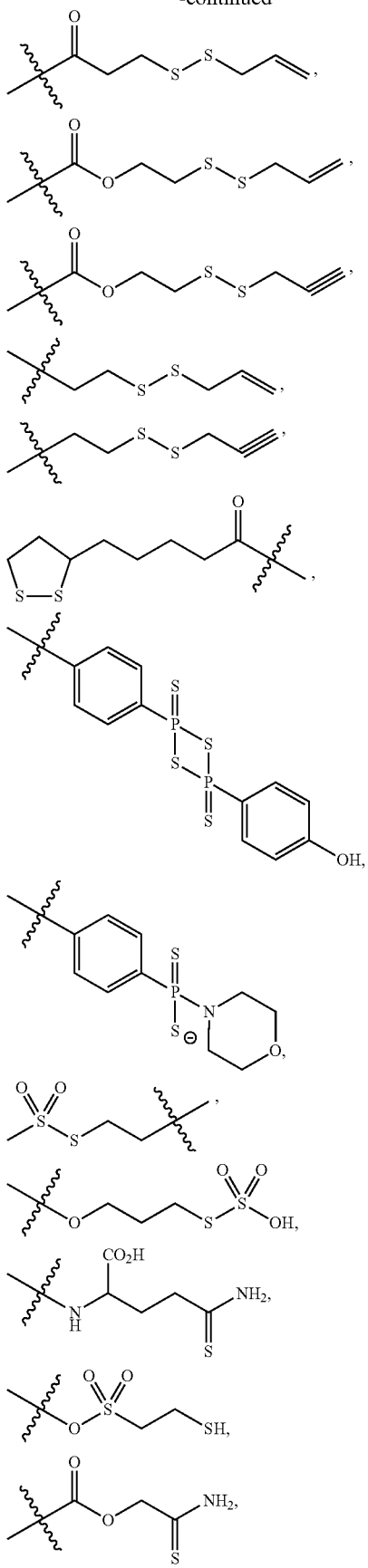
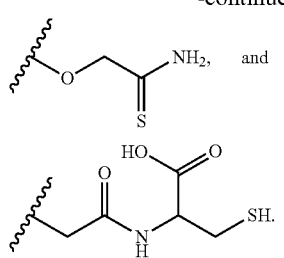
3. A compound according to claim 1, wherein X is —(CH$_2$)$_2$—S—S—(CH$_2$)$_2$—, —(CH$_2$)$_2$—S—S—S—(CH$_2$)$_2$—, or —(CH$_2$)$_2$—S—S—S—S—(CH$_2$)$_2$—.
4. A compound according to claim 1, wherein Y is —OP(O)(OEt)$_2$.
5. A compound having the structure
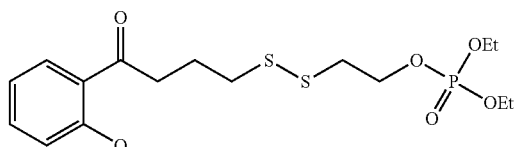
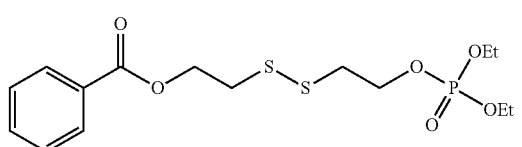
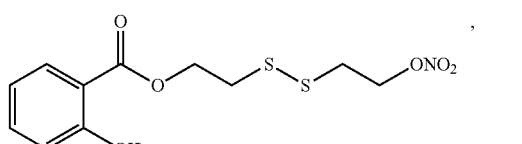
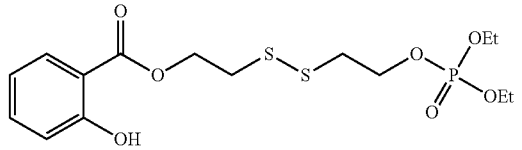
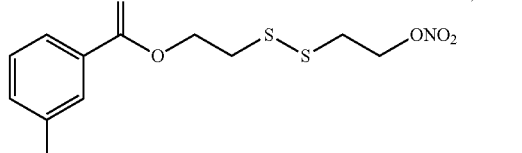

-continued

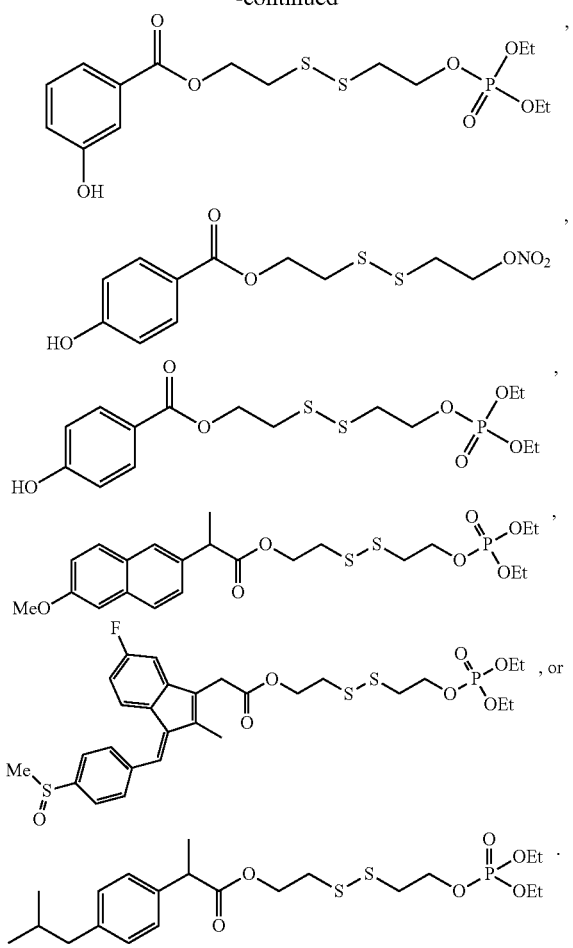

6. A method of treating an inflammatory disease, comprising administering to a subject in need thereof, an effective amount of a compound selected from the group consisting of (1) a compound of Formula I:

$$R-X-Y \quad (I)$$

wherein:
R is aspirin;
X is a cycloalkyl, an aryl, or $-(CH_2)_{n1}-S_{n2}-(CH_2)_{n1}-$;
n1 is independently an integer from 1 to 20;
n2 is 2, 3, or 4;
Y is independently $-OP(O)(OEt)_2$,

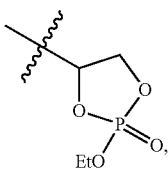 [SMILES: *C1COP(=O)(OCC)O1]

$-OSO_2R^2$, $-OSO_2OR^2$, $-OB(OR^2)_2$, or an $H_2S$ releasing moiety;
$R^2$ is independently $-(CH_2)_{n1}-H$;
cycloalkyl groups are carbocyclic or heterocyclic, fused or unfused, non-aromatic ring systems having a total of 3-16 ring members including substituent rings;

cycloalkyl groups may be unsubstituted or substituted with one or more substituent at any position;
aryl groups are carbocyclic or heterocyclic;
aryl groups may be unsubstituted or substituted with one or more substituent at any position;
cycloalkyl substituents are halo, hydroxyl, $OR^3$, $SR^3$, $NH_2$, $NHR^3$, alkyl, cycloalkyl, or aryl;
aryl substituents are halo, hydroxyl, $OR^3$, $SR^3$, $NH_2$, $NHR^3$, alkyl, cycloalkyl, aryl, nitro, carboxyl, or $-O-C(O)$-alkyl;
heterocyclic cycloalkyl and aryl groups have at least one heteroatom selected from oxygen, nitrogen, and sulfur;
$R^3$ represents alkyl, cycloalkyl, aryl, or halo;
alkyl groups are branched or unbranched, saturated or unsaturated, and have 1-20 carbon atoms in their longest chain; and
halo substituents are fluoro, chloro, or bromo;

(2) a compound of Formula I:

$$R-X-Y \quad (I)$$

wherein:
R is aspirin;
X is an alkyl, a cycloalkyl, an aryl, or $-(CH_2)_{n1}-S_{n2}-(CH_2)_{n1}-$;
n1 is independently an integer from 1 to 20;
n2 is 2, 3, or 4;
Y is independently $-OSO_2R^2$, $-OSO_2OR^2$, $-OB(OR^2)_2$, or an $H_2S$ releasing moiety;
$R^2$ is independently $-(CH_2)_{n1}-H$;
alkyl groups are branched or unbranched, saturated or unsaturated, and have 1-20 carbon atoms in their longest chain;
cycloalkyl groups are carbocyclic or heterocyclic, fused or unfused, non-aromatic ring systems having a total of 3-16 ring members including substituent rings;
aryl groups are carbocyclic or heterocyclic;
aryl groups may be unsubstituted or substituted with one or more substituent at any position;
each alkyl or cycloalkyl, independently, may be unsubstituted or substituted with one or more substituent at any position;
alkyl substituents are halo, hydroxyl, $OR^3$, $SR^3$, $NH_2$, $NHR^3$, cycloalkyl, or aryl;
cycloalkyl substituents are halo, hydroxyl, $OR^3$, $SR^3$, $NH_2$, $NHR^3$, alkyl, cycloalkyl, or aryl;
aryl substituents are halo, hydroxyl, $OR^3$, $SR^3$, $NH_2$, $NHR^3$, alkyl, cycloalkyl, aryl, nitro, carboxyl, or $-O-C(O)$-alkyl;
heterocyclic cycloalkyl and aryl groups have at least one heteroatom selected from oxygen, nitrogen, and sulfur;
$R^3$ represents alkyl, cycloalkyl, aryl, or halo; and
halo substituents are fluoro, chloro, or bromo; and (3) a compound having the structure:

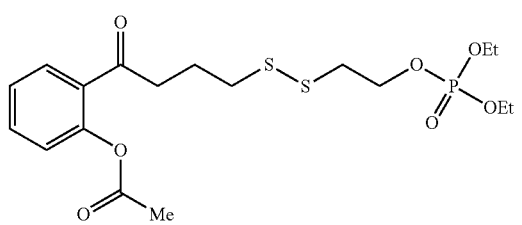

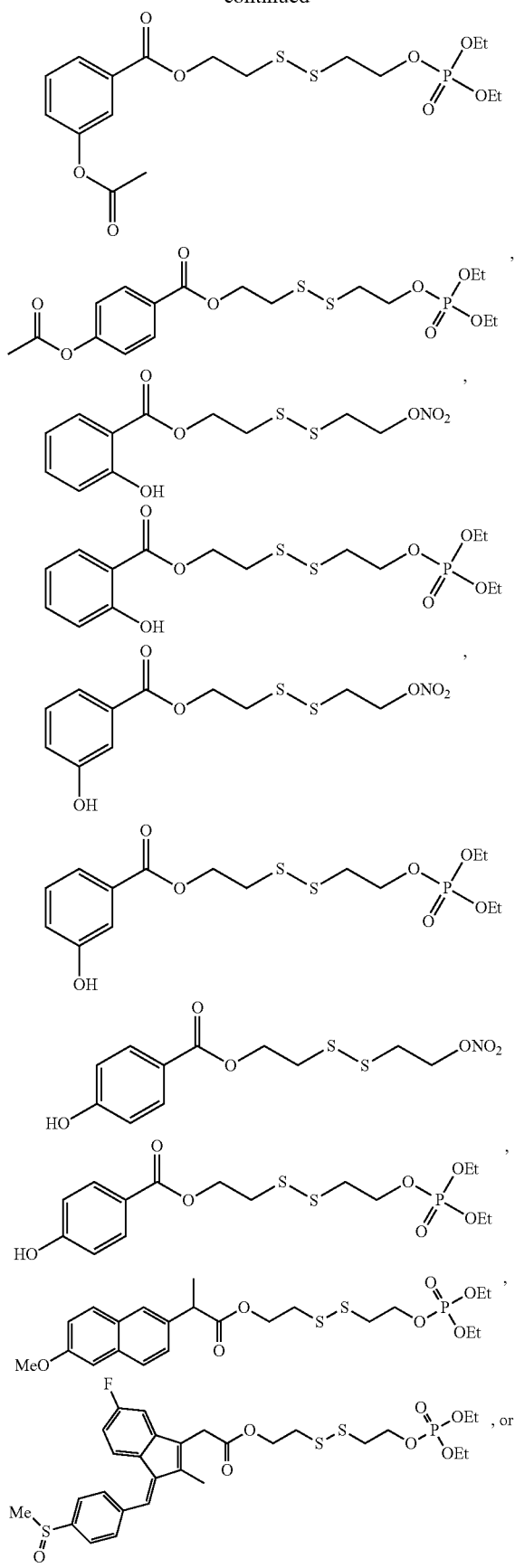

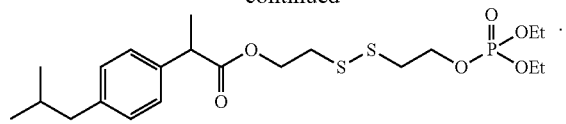

7. The method according to claim 6, wherein the inflammatory disease is cancer, rheumatoid arthritis, intestine inflammation, stomach ulcer, a cardiovascular disease, or a neurodegenerative disease.

8. A pharmaceutical composition comprising a compound selected from the group consisting of
(1) a compound of Formula I:

$$R-X-Y \qquad (I)$$

wherein:
R is aspirin;
X is a cycloalkyl, an aryl, or $-(CH_2)_{n1}-S_{n2}-(CH_2)_{n1}-$;
n1 is independently an integer from 1 to 20;
n2 is 2, 3, or 4;
Y is independently $-OP(O)(OEt)_2$,

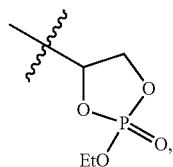 [SMILES: *C1COP(=O)(OCC)O1]

$-OSO_2R^2$, $-OSO_2OR^2$, $-OB(OR^2)_2$, or an $H_2S$ releasing moiety;
$R^2$ is independently $-(CH_2)_{n1}-H$;
cycloalkyl groups are carbocyclic or heterocyclic, fused or unfused, non-aromatic ring systems having a total of 3-16 ring members including substituent rings;
cycloalkyl groups may be unsubstituted or substituted with one or more substituent at any position;
aryl groups are carbocyclic or heterocyclic;
aryl groups may be unsubstituted or substituted with one or more substituent at any position;
cycloalkyl substituents are halo, hydroxyl, $OR^3$, $SR^3$, $NH_2$, $NHR^3$, alkyl, cycloalkyl, or aryl;
aryl substituents are halo, hydroxyl, $OR^3$, $SR^3$, $NH_2$, $NHR^3$, alkyl, cycloalkyl, aryl, nitro, carboxyl, or $-O-C(O)$-alkyl;
heterocyclic cycloalkyl and aryl groups have at least one heteroatom selected from oxygen, nitrogen, and sulfur;
$R^3$ represents alkyl, cycloalkyl, aryl, or halo;
alkyl groups are branched or unbranched, saturated or unsaturated, and have 1-20 carbon atoms in their longest chain; and
halo substituents are fluoro, chloro, or bromo;
(2) a compound of Formula I:

$$R-X-Y \qquad (I)$$

wherein:
R is aspirin;
X is an alkyl, a cycloalkyl, an aryl, or $-(CH_2)_{n1}-S_{n2}-(CH_2)_{n1}-$;
n1 is independently an integer from 1 to 20;
n2 is 2, 3, or 4;

Y is independently —OSO$_2$R$^2$, —OSO$_2$OR$^2$, —OB(OR$^2$)$_2$ or an H$_2$S releasing moiety;

R$^2$ is independently —(CH$_2$)$_{n1}$—H;

alkyl groups are branched or unbranched, saturated or unsaturated, and have 1-20 carbon atoms in their longest chain;

cycloalkyl groups are carbocyclic or heterocyclic, fused or unfused, non-aromatic ring systems having a total of 3-16 ring members including substituent rings;

aryl groups are carbocyclic or heterocyclic;

aryl groups may be unsubstituted or substituted with one or more substituent at any position;

each alkyl or cycloalkyl, independently, may be unsubstituted or substituted with one or more substituent at any position;

alkyl substituents are halo, hydroxyl, OR$^3$, SR$^3$, NH$_2$, NHR$^3$, cycloalkyl, or aryl;

cycloalkyl substituents are halo, hydroxyl, OR$^3$, SR$^3$, NH$_2$, NHR$^3$, alkyl, cycloalkyl, or aryl;

aryl substituents are halo, hydroxyl, OR$^3$, SR$^3$, NH$_2$, NHR$^3$, alkyl, cycloalkyl, aryl, nitro, carboxyl, or —O—C(O)-alkyl;

heterocyclic cycloalkyl and aryl groups have at least one heteroatom selected from oxygen, nitrogen, and sulfur;

R$^3$ represents alkyl, cycloalkyl, aryl, or halo; and halo substituents are fluoro, chloro, or bromo; and (3) a compound having the structure:

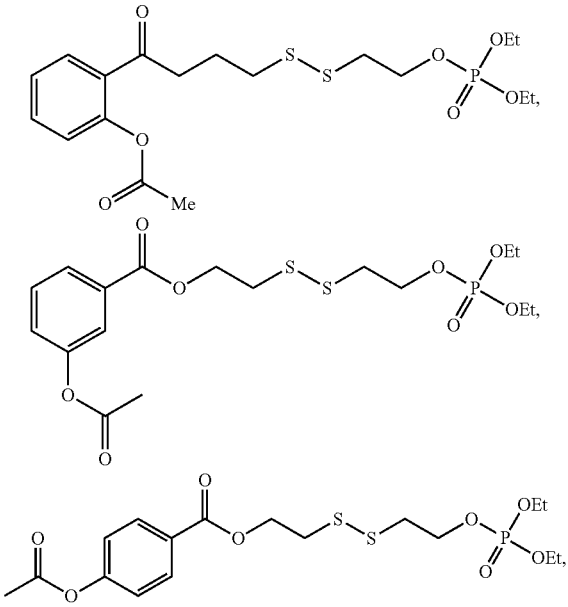

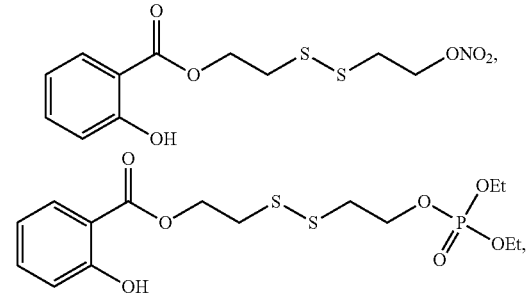

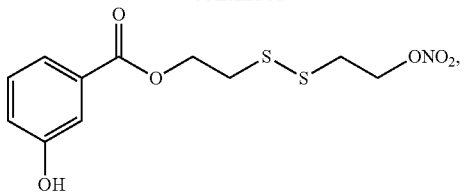

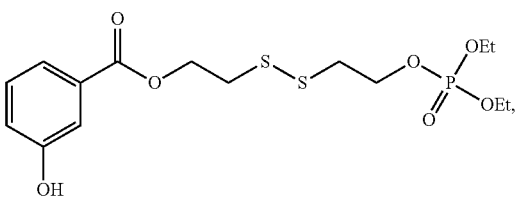

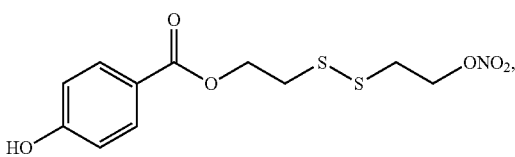

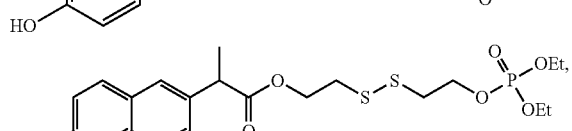

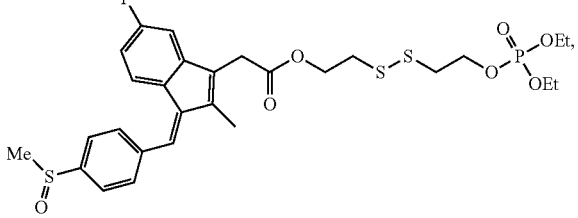

or

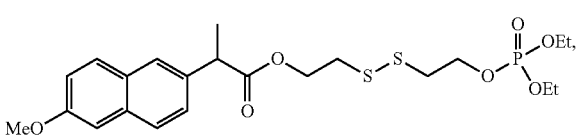

and a pharmaceutically acceptable carrier.

9. A compound of Formula I:

R—X—Y        (I)

wherein:

R is aspirin;

X is —(CH$_2$)$_{n1}$—S$_{n2}$—(CH$_2$)$_{n1}$—;

n1 is independently an integer from 1 to 20;

n2 is 2, 3, or 4;

Y is an H₂S releasing moiety selected from the group consisting of
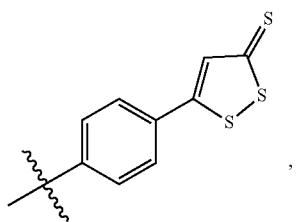
,
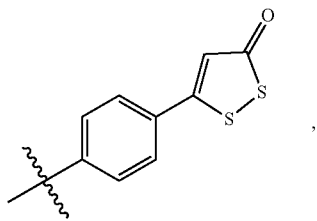
,
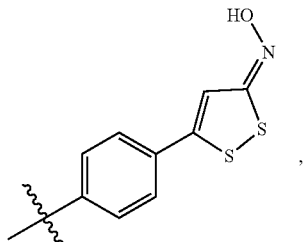
,
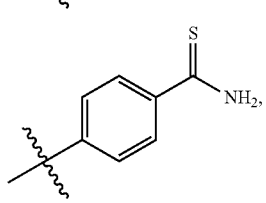
,
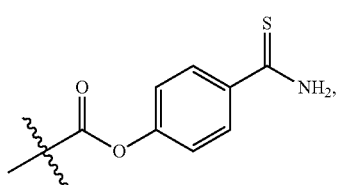
,
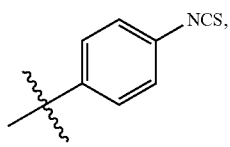
,
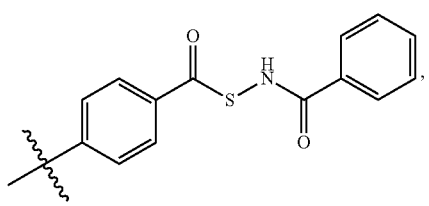
,
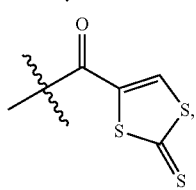
,
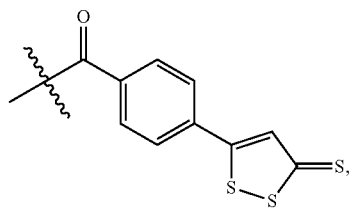
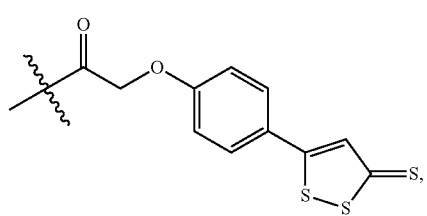
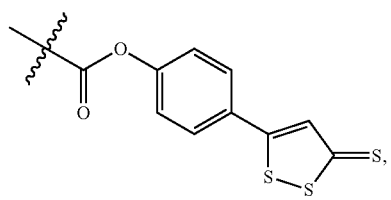
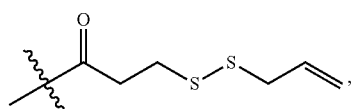
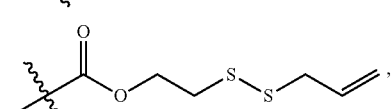
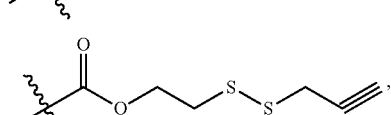
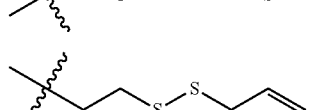
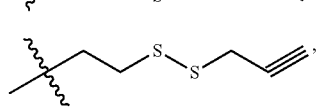
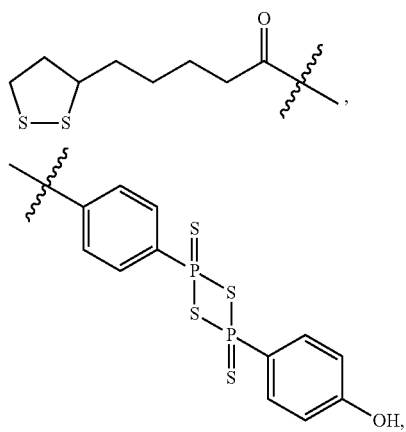

-continued

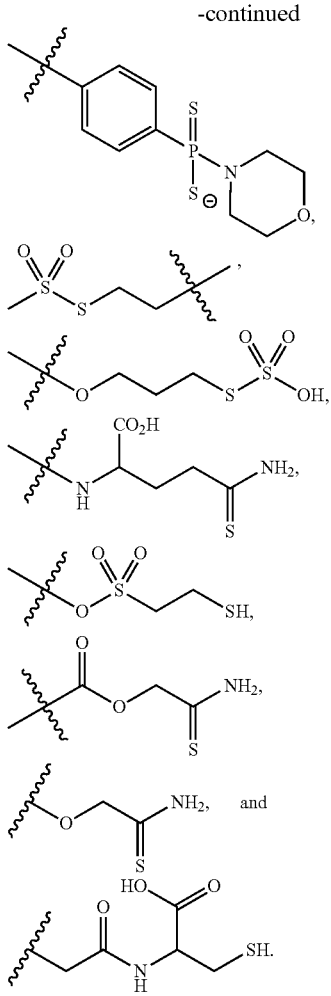

10. A compound of Formula I:

R—X—Y  (I)

wherein:
R is aspirin;
X is —(CH$_2$)$_{n1}$—S$_{n2}$—(CH$_2$)$_{n1}$—;
n1 is independently an integer from 1 to 20;
n2 is 2, 3, or 4; and
Y is —OP(O)(OEt)$_2$.

11. A compound of Formula I:

R—X—Y  (I)

wherein:
R is aspirin;
X is an alkyl, a cycloalkyl, an aryl, or —(CH$_2$)$_{n1}$—S$_{n2}$—(CH$_2$)$_{n1}$—;
n1 is independently an integer from 1 to 20;
n2 is 2, 3, or 4;
Y is independently —OSO$_2$R$^2$, —OSO$_2$OR$^2$, —OB(OR$^2$)$_2$, or an H$_2$S releasing moiety;
R$^2$ is independently [—(CH$_2$)$_{n1}$—H];
alkyl groups are branched or unbranched, saturated or unsaturated, and have 1-20 carbon atoms in their longest chain;
cycloalkyl groups are carbocyclic or heterocyclic, fused or unfused, non-aromatic ring systems having a total of 3-16 ring members including substituent rings;
aryl groups are carbocyclic or heterocyclic;
aryl groups may be unsubstituted or substituted with one or more substituent at any position;
each alkyl or cycloalkyl, independently, may be unsubstituted or substituted with one or more substituent at any position;
alkyl substituents are halo, hydroxyl, OR$^3$, SR$^3$, NH$_2$, NHR$^3$, cycloalkyl, or aryl;
cycloalkyl substituents are halo, hydroxyl, OR$^3$, SR$^3$, NH$_2$, NHR$^3$, alkyl, cycloalkyl, or aryl;
aryl substituents are halo, hydroxyl, OR$^3$, SR$^3$, NH$_2$, NHR$^3$, alkyl, cycloalkyl, aryl, nitro, carboxyl, or —O—C(O)-alkyl;
heterocyclic cycloalkyl and aryl groups have at least one heteroatom selected from oxygen, nitrogen, and sulfur;
R$^3$ represents alkyl, cycloalkyl, aryl, or halo; and
halo substituents are fluoro, chloro, or bromo.

12. A compound according to claim 11, wherein the H$_2$S releasing moiety is selected from the group consisting of